(12) United States Patent
Nachaegari et al.

(10) Patent No.: US 9,375,437 B2
(45) Date of Patent: Jun. 28, 2016

(54) PROGESTERONE CONTAINING ORAL DOSAGE FORMS AND KITS

(71) Applicant: Lipocine Inc., Salt Lake City, UT (US)

(72) Inventors: Satish Kumar Nachaegari, Salt Lake City, UT (US); Chandrashekar Giliyar, Salt Lake City, UT (US); Chidambaram Nachiappan, Sandy, UT (US); Mahesh V. Patel, Salt Lake City, UT (US); Srinivasan Venkateshwaran, Salt Lake City, UT (US)

(73) Assignee: LIPOCINE INC., Salt Lake City, UT (US)

( * ) Notice: Subject to any disclaimer, the term of this patent is extended or adjusted under 35 U.S.C. 154(b) by 0 days.

(21) Appl. No.: 13/644,929

(22) Filed: Oct. 4, 2012

(65) Prior Publication Data

US 2013/0029947 A1 Jan. 31, 2013

Related U.S. Application Data

(63) Continuation of application No. 13/204,562, filed on Aug. 5, 2011, which is a continuation of application No. PCT/US2011/041123, filed on Jun. 20, 2011.

(51) Int. Cl.

| | |
|---|---|
| A61K 31/56 | (2006.01) |
| A01N 45/00 | (2006.01) |
| A61K 31/57 | (2006.01) |
| A61K 9/20 | (2006.01) |
| A61K 9/24 | (2006.01) |
| A61K 9/28 | (2006.01) |
| A61K 9/48 | (2006.01) |

(52) U.S. Cl.
CPC ............. *A61K 31/57* (2013.01); *A61K 9/209* (2013.01); *A61K 9/2018* (2013.01); *A61K 9/2846* (2013.01); *A61K 9/4808* (2013.01); *A61K 9/4858* (2013.01); *A61K 9/2077* (2013.01)

(58) Field of Classification Search
USPC .......................................................... 514/177
See application file for complete search history.

(56) References Cited

U.S. PATENT DOCUMENTS

| | | |
|---|---|---|
| 3,164,520 A | 1/1965 | Raymond |
| 4,196,188 A | 4/1980 | Besins |
| 4,230,702 A | 10/1980 | Eckert et al. |
| 4,439,432 A | 3/1984 | Peat |
| 5,057,319 A | 10/1991 | Gottwald et al. |
| 5,140,021 A | 8/1992 | Maxson |
| 5,543,150 A | 8/1996 | Bologna et al. |
| 5,620,705 A | 4/1997 | Dong et al. |
| 5,633,011 A | 5/1997 | Dong et al. |
| 5,645,856 A | 7/1997 | Lacy |
| 5,770,227 A | 6/1998 | Dong et al. |
| 5,948,766 A | 9/1999 | Milan et al. |
| 6,086,916 A | 7/2000 | Agnus |
| 6,096,338 A | 8/2000 | Lacy |
| 6,117,450 A | 9/2000 | Dittgen et al. |
| 6,294,192 B1 | 9/2001 | Patel |
| 6,500,814 B1 | 12/2002 | Hesch |
| 6,544,553 B1 | 4/2003 | Hsia et al. |
| 6,602,521 B1 | 8/2003 | Ting et al. |
| 6,656,929 B1 | 12/2003 | Agnus et al. |
| 6,866,865 B2 | 3/2005 | Hsia et al. |
| 6,923,988 B2 | 8/2005 | Patel et al. |
| 7,431,941 B2 | 10/2008 | Besins et al. |
| 7,473,687 B2 * | 1/2009 | Hoffman et al. ............... 514/182 |
| 7,943,602 B2 * | 5/2011 | Bunschoten et al. .......... 514/171 |
| 7,976,871 B2 * | 7/2011 | Vaya et al. ..................... 424/469 |
| 8,133,507 B2 | 3/2012 | Yum et al. |
| 8,951,996 B2 | 2/2015 | Giliyar et al. |
| 2002/0131988 A1 | 9/2002 | Foster et al. |
| 2003/0077297 A1 | 4/2003 | Chen et al. |
| 2003/0236236 A1 | 12/2003 | Chen et al. |
| 2004/0052824 A1 | 3/2004 | Abou Charca-Vernet et al. |
| 2004/0131553 A1 | 7/2004 | Besse |
| 2004/0266025 A1 | 12/2004 | Hickok et al. |
| 2006/0009509 A1 | 1/2006 | Grubb et al. |
| 2006/0275360 A1 | 12/2006 | Ahmed et al. |
| 2008/0188829 A1 | 8/2008 | Creasy |
| 2009/0098200 A1 | 4/2009 | Temtsin Krayz et al. |
| 2009/0123534 A1 | 5/2009 | Besins et al. |
| 2009/0264395 A1 | 10/2009 | Creasy |

(Continued)

FOREIGN PATENT DOCUMENTS

| | | |
|---|---|---|
| CN | 1398590 A | 2/2003 |
| CN | 1446540 A | 10/2003 |

(Continued)

OTHER PUBLICATIONS

De Lignieres, B. "Oral Micronized Progesterone". Clinical Therapeutics vol. 21, No. 1, 1999, pp. 41-60.*
17-Hydroxyprogesterone; Wikipedia, The Fee Encyclopedia; http://en.wikipedia.org/wiki/17-Hydroxyprogesterone; as accessed Apr. 22, 2011; 5 pages.
Saxton et al; Reproductive Biology and Endocrinology; 2004; vol. 2, No. 80.
Greene; Progesterone and Preterm Delivery—Déjà Vu All Over Again; NJEM; Jun. 12, 2003; pp. 2453-2455, vol. 348, No. 24.
Levy et al.; Pharmacokinetics of Natural Progesterone Administered in the Form of a Vaginal Tablet; Human Reproduction; Mar. 1999; pp. 606-610; vol. 14, No. 3.

(Continued)

*Primary Examiner* — Layla Soroush
(74) *Attorney, Agent, or Firm* — Jonathan Baker

(57) ABSTRACT

The present invention provides for progesterone containing pharmaceutical oral dosage forms, pharmaceutical kits, and related methods. In one embodiment, an oral dosage form formulated for on-going administration is provided. The oral dosage form includes an amount of progesterone and a pharmaceutically acceptable carrier. The oral dosage form is formulated such that upon single dose administration to a non-pregnant woman in follicular phase, the oral dosage form provides a serum progesterone $C_{24h}$ of at least 0.20 ng/mL.

62 Claims, 5 Drawing Sheets

(56) References Cited

U.S. PATENT DOCUMENTS

| | | | |
|---|---|---|---|
| 2011/0152840 | A1 | 6/2011 | Lee et al. |
| 2011/0312927 | A1* | 12/2011 | Nachaegari et al. .......... 514/177 |
| 2012/0148675 | A1 | 6/2012 | Chickmath et al. |
| 2013/0023505 | A1 | 1/2013 | Garfield et al. |

FOREIGN PATENT DOCUMENTS

| | | |
|---|---|---|
| CN | 1509720 A | 7/2004 |
| CN | 1623550 A | 6/2005 |
| JP | 2004/155780 A | 6/2004 |
| JP | 2006-524238 | 10/2006 |
| WO | WO 90/08537 A1 | 8/1990 |
| WO | WO 93/12797 A1 | 7/1993 |
| WO | WO 95/05807 A1 | 3/1995 |
| WO | WO 00/59482 A1 | 10/2000 |
| WO | WO 03/077923 A1 | 9/2003 |
| WO | WO 2004/080438 A1 | 9/2004 |
| WO | WO 2006/128057 A2 | 11/2006 |
| WO | WO 2009/070794 | 6/2009 |
| WO | WO 2010/117873 A2 | 10/2010 |
| WO | WO 2011-053666 | 5/2011 |

OTHER PUBLICATIONS

O'Brien et al; Progesterone Vaginal Gel for the Reduction of Recurrent Preterm Birth: Primary Results From a Randomized, Double-Blind, Placebo-Controlled Trial; Ultrasound Obstet Gynecol; Oct. 2007; pp. 687-696; vol. 30, No. 5.
Defranco et al; Vaginal Progesterone is Associated with a Decrease in Risk for Early Preterm Birth and Improved Neonatal Outcome in Women with a Short Cervix: A Secondary Analysis from a Randomized, Double-Blind; Placebo-Controlled Trial; Ultrasound Obset Gynecol; Oct. 2007; pp. 697-705; vol. 30, No. 5.
Rai et al.; Oral Micronized Progesterone for Prevention of Preterm Birth; Int J Gynaecol Obstet; Jan. 2009, pp. 40-43; vol. 104, No. 1.
PCT Application PCT/US2011/041123; filing date Jun. 20, 2011; Satish Kumar Nachaegari; International Search Report mailed Feb. 21, 2012.
U.S. Appl. No. 12/819,125, filed Jun. 18, 2010; Satish Kumar Nachaegari.
U.S. Appl. No. 13/193,571, filed Jul. 28, 2011; Chandrashekar Giliyar; office action dated Nov. 8, 2012.
17alpha Hydroxyprogesterone Caproate for Prevention of Preterm birth, FDA, 0, Aug. 2, 2006 (see introduction).
PCT/US2012/049602; Filed Aug. 3, 2012; Lipocine Inc., et al.; international search report dated Jan. 29, 2013.
PCT/US2012/048708; Filed Jul. 27, 2012; Lipocine Inc., et al.; international search report dated Feb. 15, 2013.
Benzyl Benzoate data sheet; Emerald Kalama Vemical; CAS Registration No. 120-51-4.
PCT Application PCT/US2013/063584; filing date Oct. 4, 2013; Lipocine Inc.; International Search Report mailed Mar. 21, 2014.
Rogers, et al.; Micronized powders of a poorly water soluble drug produced by a spray-freezing into liquid-emulsuion process; European Journal of Pharmaceutics and Biopharmaceutics; 2003; pp. 161-172; vol. 55; Elsevier Science B.V.
U.S. Appl. No. 13/193,571, filed Jul. 28, 2011; Chandraskekar Gilyar; office action dated Apr. 23, 2014.
EP Application 12822217.1; Filing date Aug. 3, 2012; Lipocine Inc.; European Search Report dated Feb. 23, 2015.
EP application 12818254.0; filing date Jan. 31, 2013; Lipocine Inc.; European Search Report dated Nov. 20, 2014.
U.S. Appl. No. 13/029,989, filed Feb. 17, 2011; Feng-Jing Chen; office action dated Nov. 18, 2013.
U.S. Appl. No. 12/957,206, filed Nov. 30, 2010; Chanddrashekar Gilyar; office action dated Jul. 18, 2013.
U.S. Appl. No. 12/326,7111, filed Dec. 2, 2008; Mahesh Patel; office action dated Jul. 19, 2013.
U.S. Appl. No. 13/193,571, filed Jul. 28, 2011; Chandrashekar Gilyar; notice of allowance mailed Aug. 1, 2014.
U.S. Appl. No. 14/801,737, filed Jul. 16, 2015; Chandrashekar Giliyar; Office Action dated Aug. 19, 2015.
U.S. Appl. No. 14/633,545, filed Feb. 27, 2015; Chandrashekar Giliyar; Office Action dated Aug. 20, 2015.
U.S. Appl. No. 14/633,545, filed Feb. 27, 2015; Chandrashekar Giliyar; Notice of Allowance dated Oct. 7, 2015.
U.S. Appl. No. 14/261,057, filed Apr. 24, 2014; Chandrashekar Giliyar; Office Action dated Nov. 5, 2015.
U.S. Appl. No. 14/477,771, filed Sep. 4, 2014; Chandrashekar Giliyar; Office Action dated Nov. 6, 2015.
Notice of Allowance for U.S. Appl. No. 14/261,057 dated Feb. 12, 2016, 9 pages.
Notice of Allowance for U.S. Appl. No. 14/801,737 dated Feb. 18, 2016, 8 pages.
Office Action for U.S. Appl. No. 14/801,737 dated Nov. 16, 2015, 17 pages.
Thevenet et al, "Progesterone for Preterm Birth Prevention: An Evolving Intervention", American Journal of Obstetrics and Gynecology, Mar. 2009, pp. 219-224.

\* cited by examiner

PROGESTERONE CONTAINING ORAL DOSAGE FORMS AND KITS

This application is a continuation-in-part of U.S. patent application Ser. No. 13/204,562, filed Aug. 5, 2011, which is a continuation of PCT/US2011/041123, filed on Jun. 20, 2011, which claims the benefit of U.S. patent application Ser. No. 12/819,125, filed on Jun. 18, 2010, each of which is incorporated herein by reference.

FIELD OF THE INVENTION

The present invention relates to progesterone compositions, oral dosage forms and associated methods. Accordingly, this invention involves the fields of chemistry, pharmaceutical sciences, medicine and other health sciences.

BACKGROUND OF THE INVENTION

Progesterone (pregn-4-ene-3,20-dione) is a C-21 steroid hormone involved in the female menstrual cycle, pregnancy (supports gestation), and embryogenesis of humans and other species. Progesterone belongs to a class of hormones called progestogens, and is the major naturally occurring human progestogen. Progesterone can be used alone, or in combination with estrogenic agents, to provide a hormonal state in women through hypothalamic, pituitarian, and some endometrial effects to enable contraception and some non-contraception indications, such as endometriosis, regular menstrual cycles, improvement in acne, dysmenorrhea and premenstrual symptoms such as dysphoric disorder, also known as PMDD, polycystic ovarian syndrome (PCOS), perimenopause, hirsutism (undesired body or facial hair growth). Although quite effective, oral hormonal contraceptive use is generally characterized by poor adherence and relatively high discontinuation. The primary objective of contraception is to achieve an anovulatory state with acceptable menstrual cycle characteristics and side effect profile.

Progesterone's role in contraception is primarily through prevention of ovulation by suppressing follicle stimulating hormone (FSH) and luteinizing hormone (LH), preventing implantation of fertilized ovum by suppressing endometrium development, and to thicken cervical mucus making sperm penetration difficult. Synthetic or natural estrogen, if used in combination with a progestogen, provides better cycle control and prevents estrogen deficiency due to decreased secretion of endogenous estrogen from the follicle. Estrogen inhibits FSH release from the anterior pituitary to prevent selection of dominant follicle, to provide stability to endometrium, to decrease rate of breakthrough bleeding, to thin cervical mucus, and to increase expression of progesterone receptors.

Progestogen only pills (POPs) for oral contraception are typically started on days 1 to 5 of the menstrual cycle and particularly suited for women who are smokers and over 35 years old, overweight or obese, over the age of 45, diabetic, prone to chloasmia, intolerant to estrogen, nursing mothers, prone to migraine with aura, and have hypertension. Currently, combination (progestogen plus estrogen) oral contraceptive (COC) pills are most preferred due to reportedly more reliable efficacy if used as directed, they have better cycle control and are more forgiving with respect to missed dose related safety margins associated with contraception failure. In contrast, commercially available progestogen-only oral contraceptives must be taken at nearly the exact same time every day to reduce the risk of contraceptive failure with "missed dose" related safety margin of only a few hours.

Orally-administered progesterone undergoes several successive metabolic steps in the gut, intestinal wall, and liver. The first step is the contact with intestine bacteria which has $5\alpha$ reductase activity, then with the intestinal wall, predominantly the upper gastro-intestinal wall which has $5\alpha$-reductase activity and also initiates conjugation of steroids with glucuronic acid. The second step is the contact with liver enzymes after circulation in the portal vascular systems. Liver cells in women express mainly $5\alpha$-reductase, $3\alpha$ and $20\alpha$-hydroxylase activities. $3\alpha$-OH-$5\alpha$-pregnan-20-one is known as allopregnanolone and $3\alpha$-OH-$5\alpha$-pregnan-20-one is known as pregnanolone. Both of the metabolites can be collectively addressed as "pregnane" metabolites. Pregnane metabolites are neurosteroids and are active agonists on the Gamma Amino Butyric Acid-A ($GABA_A$) receptor unlike progesterone per se. High doses of $GABA_A$ receptor agonists such as pregnane metabolites induce dizziness, sedation, hypnosis, and anxiolysis, and are antiepileptic. Therefore, reduced level of pregnane metabolites provides acceptable progesterone therapy without significant adverse events such as sedation, dizziness and hypnosis.

Synthetic combination oral contraceptives also have higher cardiovascular risk such as ischemic stroke, venous thromboembolism (VTE), myocardial infarction, arterial hypertension. It has been suggested that COC's may contribute to the risk of breast cancer in a woman. These side effects and increased risks are associated with, progestin and/or estrogen, its relative doses, or the recommended dosing regimen. Overall, the lack of high selectivity/specificity of synthetic progestins to progesterone receptors, estrogenic action and/or anti-estrogenic action, antimineralocorticoid activity, androgenic action and/or anti androgenic action, appear to be associated with varying intensities of the side effects. Unlike some synthetic progestins like gestodene, levonorgesterol, etc. natural progesterone has low binding affinities to human sex hormone binding globulin (SHBG). Progestins having anti-androgenicity effects could result in loss of libido and compromised sexual health. This can be particularly true when they are combined with ethinyl estradiol. This effect is primarily due to androgen insufficiency through direct inhibition of androgen production in the ovaries and by a marked increase in the hepatic synthesis of SHBG, which is known to bind to circulating testosterone making it less bioavailable. Increases in SHBG values as high as 400% have been reported in users of ethinyl estradiol based combination oral contraception as compared to women who never used combination oral contraception.

The delivery of progesterone via oral route in a suitable way for contraception and non-contraception use still remains a challenge given its extensive metabolism to neurosteroids. With this in mind, research continues to develop natural progesterone oral dosage forms that can be used to effectively provide contraceptive and non-contraceptive activity without having the negative side-effects associated with synthetic progestins.

Currently, ethinyl estradiol (EE) is the most utilized estrogen in a combination oral pill with androgenic progestin such as levonorgestrel (e.g. Lybrel®) or anti-androgenic progestin such as drosperinone (e.g. Yaz® and Yasmin®). Estrone producing bioidentical 17-estradiol or its ester prodrug, estradiol valerate, is also commonly combined with progestins in combination oral pills, e.g. Natazia® with dienogest/estradiol valerate, Zoely® with nomegestrol acetate with 17-estradiol), and presumably have less hepatic effect compared to EE containing combinations. However, their use in combination may provide cycle management challenges that need to be offset by proper choice of progestin, balance of progestin to estrogen, and multitude of dosing regimens for acceptable cycle control. A combination of estradiol and norethindrone acetate is available for non-contraception treatment of moderate to severe vasomotor symptoms associated with menopause, prevention of postmenopausal osteoporosis, and treatment of moderate to severe symptoms of vulvar and vaginal atrophy associated with menopause.

Currently, the only known POP contraceptive pills are in the form of anti-androgenic desogestrel sold outside the U.S. as Cerazette® with a 12 hour "missed dose" related safety margin to prevent contraception failure and androgenic norethindrone sold as Micronor® in US with a 3 hour "missed dose" related safety margin for contraception failure, or androgenic levonorgestrel sold as Microlut®. Most available combination pill contain anti-androgenic progestins such as drospirenone and dinogest, or androgenic levogersterol, and norethindrone. Normegesterol acetate (NOMAC), a non-androgenic and non-anti-androgenic progestin with a long half-life is devoid of anti-mineralocorticoid activity, which is critical to manage metabolic side effects. It is also known that progestins with stronger androgenic activity have a stronger negative impact on lipid metabolism.

The sub-optimal half-life of synthetic androgenic or anti-androgenic progestins present challenges w.r.t. to pill amenorrhea due to very long half-life in women who desire to bleed at least few times a year to ascertain their reproductive health and time to reversibility (e.g. ~7 days with drosperinone-containg pills) in case of contraception cessation and wanting to become pregnant without risking progestin effects on the fetus. While shorter half progestins have favorable pill amenorrhea and reversibility profile they also result in a shorter missed dose safety margin of 3 hr and lower efficacy due to lower anovulation rates (~50%) such as with norethindrone.

SUMMARY OF THE INVENTION

The present invention provides for progesterone containing pharmaceutical oral dosage forms, pharmaceutical kits, and related methods. In one embodiment, an oral dosage form formulated for on-going administration is provided. The oral dosage form can include an amount of progesterone and a pharmaceutically acceptable carrier. The oral dosage form is formulated such that upon single dose administration to a non-pregnant woman in follicular phase, the oral dosage form provides a serum progesterone $C_{24h}$ of at least 0.20 ng/mL.

In another embodiment, an oral dosage form for ongoing administration is provided that includes an amount of progesterone and a pharmaceutical acceptable release modulator. The oral dosage form can be formulated such that wherein upon dissolution of the oral dosage using a USP Type-1 dissolution apparatus in 900 mL of de-ionized water with 2.0% (w/v) of sodium lauryl sulfate at 100 rpm, less than 10 wt % of the progesterone is released from the dosage form after about 1 hour, 50 wt % or less of the progesterone is released in the first 6 hours and at least 70 wt % of the progesterone is released within 12 hours.

In a further embodiment, a pharmaceutical kit is provided. The kit can include a plurality of doses of a progesterone-containing oral dosage form and optionally a placebo dose of an oral dosage form. The plurality of progesterone-containing oral dosage forms can include oral dosage forms having different doses of progesterone. The kit can be such that upon single dose administration of one of the progesterone-containing oral dosage forms to a non-pregnant woman in follicular phase the menstruation cycle, the progesterone-containing oral dosage form provides a ratio of increased serum progesterone $AUC_{12-24}$ (ng*h/mL) to administered dose (mg) is at least 0.005 (ng*h/ml)/mg and does not exceed about 0.03 (ng*h/ml)/mg. Furthermore, such a kit may include a set of instructions on dosing or other information regarding a progesterone regimen using the included progesterone-containing oral dosage form along with any optional placebo doses.

In another embodiment, the oral dosage forms set forth in the above embodiments can include an estrogenic compound. In still a further embodiment, the oral dosage form is formulated such that upon attainment of steady state blood levels to a non-pregnant woman, the oral dosage form provides a serum progesterone $C_{24h}$ of at least 0.35 ng/mL

DETAILED DESCRIPTION

Figure 1:
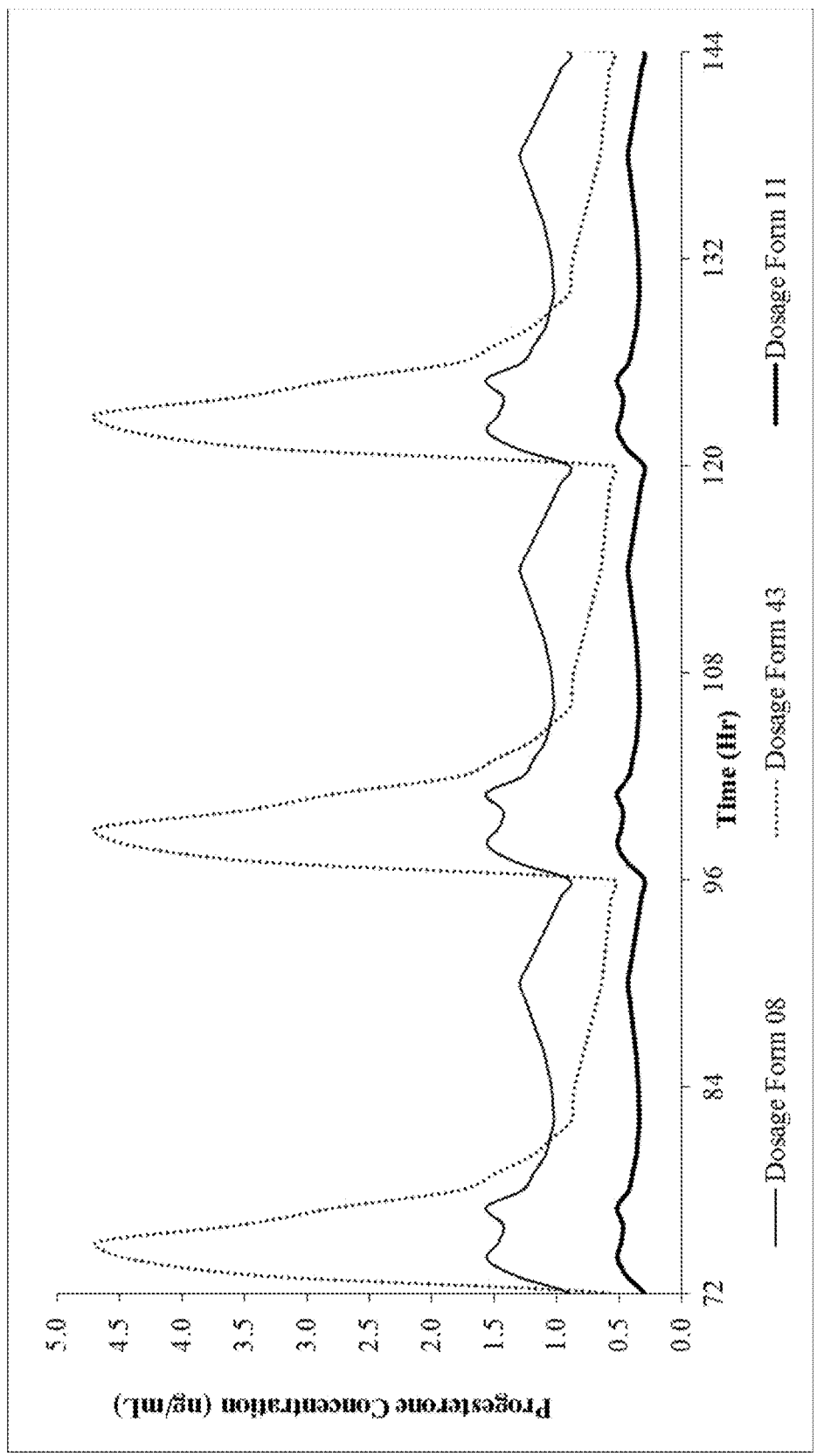
FIG. 1 shows simulated steady state concentrations of progesterone upon administration of dosage forms 8, 11 and 43 with 400 mg progesterone.

Before the present oral dosage forms and methods for the delivery and use of progesterone are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

Definitions

As used herein, "drug," "active agent," "bioactive agent," "pharmaceutically active agent," "therapeutically active agent" and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category, it is understood that such recitation is intended to include the active agent per se, as well as pharmaceutically acceptable salts, esters or compounds significantly related thereto, including without limitation, prodrugs, active metabolites, isomers, and the like, unless the context or scientific principles clearly indicate otherwise.

As used herein, the term "treatment" when used in conjunction with the administration of progesterone, refers to the administration of progesterone to subjects who are either asymptomatic or symptomatic. In other words, "treatment" can be to reduce, ameliorate, or eliminate symptoms associated with a condition or it can be prophylactic treatment, i.e. to prevent or reduce the occurrence or severity of the symptoms. Such prophylactic treatment can also be referred to as prevention of the condition.

As used herein, "treatment" also refers to a change/alteration that is brought about in a subject's typical physiological processes following administration of a drug in a given dosage form, as in case for example, contraception provided by the single or multiple dose administration of the current invention's dosage forms which result in inhibiting the ovulation phase of the typical menstrual cycle.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Furthermore, the term "dosage form" can include one or more formulation(s) or composition(s) provided in a format for administration to a subject. When any of the above terms is modified by the term "oral" such terms refer to compositions, formulations, or dosage forms formulated and intended for oral administration to subjects.

As used herein, "carrier" or "pharmaceutically acceptable carrier" refers to a substance with which a drug may be combined to achieve a specific dosage formulation or oral dosage form for delivery to a subject. In the some aspects of the present invention, the carriers used may or may not enhance drug delivery. Further, the carrier, or at least a portion thereof must be suitable for administration into a subject along with the drug.

As used herein, "subject" refers to a mammal that may benefit from the administration of a drug composition or method of this invention. In one specific aspect, a subject is a human. In another aspect, the subject is a female. In one embodiment, the subject can be a non-pregnant female or woman. In another embodiment the subject can be a non-pregnant woman in the follicular phase of the menstruation cycle.

For the purposes of the present disclosure, the term a single "menstruation cycle" has a typical duration of about 28 days. The term "follicular phase" refers to the initial phase of a woman's menstruation cycle which typically has a duration of from about day 1 to about day 10 from the start of the menses, in a normal menstruating women, this phase occurs before ovulation. The term "luteal phase" refers to the later phase of a woman's menstrual cycle which typically has a duration of from about 14-28 days, in normal menstruating women, this phase starts from about ovulation to the next menses.

The term "oral administration" represents any method of administration in which an active agent can be administered by swallowing, chewing, or sucking or drinking an oral dosage form. Such solid or liquid oral dosage forms are traditionally intended to substantially release and or deliver the active agent in the gastrointestinal tract beyond the mouth and/or buccal cavity. Examples of solid dosage forms include conventional tablets, multi-layer tablets, capsules, caplets, etc., which do not substantially release the drug in the mouth or in the oral cavity.

As used herein, the terms "release" and "release rate," are used interchangeably to refer to the discharge or liberation of a substance, including without limitation a drug, from the dosage form into a surrounding environment such as an aqueous medium either in vitro or in vivo.

As described herein, "Saccadic Eye Velocity" (SEV), a psychometric method, can be measured using the following test method: a subject's head is restrained and an light emitting object placed in front of eyes is moved to a certain angle either to left or right in front of eyes and the speed with which the eye ball moves to follow the light is measured as a function of time.

As used herein, the term "substantially free of" as it refers to the presence or lack of a particular composition or ingredient or component in a given formulation or oral dosage form refers to the complete or near complete absence of the ingredient from the formulation such that the ingredient, if present, forms only a minor component or impurity of the formulation. For example, a composition that is substantially free of edible oils may contain a small amount of edible oil impurities that may be present in commercially available surfactants or other commercially available non-edible oil compositions. In one aspect, a formulation that is substantially free of edible oils could have less than 10 wt % of edible oils present in the formulation. In another aspect, a formulation that is substantially free of oils could have less than 5 wt % of edible oils present in the formulation. In yet another aspect, a formulation that is substantially free of edible oils could have less than 2.5 wt % of edible oils present in the formulation.

As used herein, "edible oil" is any oil that can be safely consumed by a mammal. These oils will generally be selected from those oils generally regarded as safe for pharmaceutical or culinary use. Suitable edible oils for the present invention include, but are not limited to, safflower oil, linseed oil, soybean oil, corn oil, sunflower oil, sesame oil, olive oil, cottonseed oil, flaxseed oil, menhaden oil. For the purpose of this invention, the primary characteristic of an "edible oil" is that they are triglycerides of long chain fatty acids with carbon chain length of 12 to 18 and do not include oils which have carbon chain length greater than 20 such as oils containing omega fatty acids, example fish oil, flax seed oil, algae oil and the like.

The terms "release modifying agent", "release modulator", and "release modifiers" are used interchangeably and refer to pharmaceutically acceptable agents or devices that are able to alter, delay, target, increase or decrease, or otherwise customize, the release rates of at least one of the contents of the compositions or dosage form, when exposed to an aqueous use environment. With this in mind, a "hydrophilic release modulator" is a release modulator that has a tendency to bind or absorb water. This binding or absorption can result in swelling and/or the formation of reversible gels that can control the release of active agents in a dosage form. Similarly, a "lipophilic release modulator" is a release modulator that has an affinity for fats and/or oils. Within being limited by theory, some lipophilic release modulators can modify release by forming films or by slowing the erosion or digestion of an oral dosage form. A "lipidic lipophilic modulator" is a lipophilic release modulator that is an oil or fatty substance. Accordingly, a "non-lipidic lipophilic release modulator" is a lipophilic release modulator that is not an oil or fatty substance.

As used herein, the term "placebo" used to describe a dose or oral dosage form refers to a dose or oral dosage form that includes no progesterone. While the placebo oral dosage form are free of progesterone, such oral dosage forms may contain other active agents such as estrogenic agents, androgenic agents, vitamins, folic acid, pain relievers, etc.

By "osmotic agent" is meant any agent that creates a driving force for transport of water from the environment of use into the core of the dosage form.

As used herein, the terms "progesterone," "bio-identical progesterone" or "natural progesterone" are used interchangeably and refer to progesterone that has molecular and chemical properties that are the same as those of the progesterone that is naturally present in the human body, it is generally known to those skilled in art as molecule identified by CAS No. 57-83-0.

As used herein the term "bio-identical estrogenic agent" refers to an estrogenic agent whose molecular and chemical properties is identical to that of the estrogen present in the human body, it is generally known to those skilled in art as estradiol molecule identified by CAS No. 50-28-2. Bio-identical estrogenic agents can be obtained from natural sources or by chemical synthesis.

As used herein, the phrase "ongoing administration" refers to administration of an oral dosage form for a period of 10 or more consecutive days.

Steady state concentration, $C_{ss}$, corresponds to the state of equilibrium obtained at the end of a certain number of administrations. To obtain an increase in the plasma concentration with repeated administrations, it is necessary that a residual concentration persists at the time of the following administration. At the steady state, if the dose and the frequency of administrations remain constant, the concentration obtained will also be constant. The steady state is obtained at the end of approximately five half-lives As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, the terms "plasma concentration," "serum concentration," or "concentration in the blood" of a drug or drug metabolite refers to the serum concentration of the drug or drug metabolite.

Progesterone in serum can be analyzed by specific methods like LC-MS or with not very specific Radioimmunoassay (RIA) e.g. Advia Centaur® System. Unless otherwise mentioned, the pharmacokinetic (PK) concentrations and related parameters in this invention are based on LC-MS analytical methods. Similarly, pregnane metabolites in serum can be analyzed by specific methods like chromatography or the like. The determination of 5-α and 5-β pregnanolone can be performed by gas chromatography-mass spectrometry with stable isotope dilution. Briefly known amounts of deuterium labeled analogues are added to plasma samples that are then equilibrated and extracted. The extracts are purified by liquid chromatography using Sephadex LH-20, derivatized and selected ion monitoring is performed at nominal masses m/z 496 and 500, corresponding to the characteristic ions of the heptaflurobutyrates of the native and the labeled pregnanolone, respectively.

It is to be understood that any relative comparisons of blood plasma levels of any compound should be made with the same assay methodology, or corrections must be made to adjust for discrepancy for assay specificity. For example, it has been reported that the results of the serum progesterone or its metabolites determined by Radio Immuno Assay (RIA) methods could be about 8 to 10 times higher than the results obtained by the LC-MS method.

Unless otherwise mentioned, all the serum concentrations of drug and/or its metabolite(s) disclosed in the embodiments and examples herein, refer to the "observed" concentrations, (i.e. the values represent the sum of the corresponding base-line plus additional concentration due to absorption from the administered drug). Whereas, an "increase in the serum concentration" or "increased serum concentration" of the drug and/or its metabolite(s) refers to the corresponding base-line adjusted or base-line corrected concentration.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

Natural progesterone is bioidentical to endogenous progestogenic hormone produced by female reproductive organs. It is highly selective to progesterone receptors, has almost no androgenic potential, and no antiandrogenic activity. Natural progesterone also provides the benefits of anti-mineralocorticoid activity such as reduced water and sodium retention resulting in no weight gain. It is expected to have superior side effect profile with respect to thrombolytic events, breast and cervical cancers, and lower risk to fetus in case of contraception failure than synthetic progestins. Moreover, progesterone has little effect on carbohydrate metabolism compared to synthetic progestins, especially androgenic progestins. Unfortunately, natural progesterone is a weakly potent, lipophilic, and poorly water soluble steroid. Progesterone from conventional formulations and oral dosage forms, such as immediate release oral commercial product Prometrium, result in low and significantly variable bioavailability. Natural progesterone has a biological half-life of 3-5 hours with high blood level fluctuation index. Further, orally-administered progesterone undergoes several successive metabolic steps in the gut, intestinal wall, and liver which result in the formation of pregnane metabolites that can cause various undesirable side-effects. Therefore, it has been discovered that it would be desirable to provide an oral dosage form that delivers natural progesterone in less fluctuating manner while producing reduced levels of pregnane metabolites. Additionally, the presently disclosed oral dosage forms are formulated to provide acceptable "missed dose" safety margins, faster contraception reversibility, and lower potential of pill related amenhorrea.

The disclosed oral dosage forms fill the unmet need of an effective natural progesterone containing oral dosage form that can be used for both contraceptive and non-contraceptive purposes with once daily administration while reducing the negative metabolite side-effects and proving better "missed dose" safety margins.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

The present invention provides for progesterone containing pharmaceutical oral dosage forms, pharmaceutical kits, and related methods. In one embodiment, an oral dosage form formulated for on-going administration is provided. The oral dosage form includes an amount of progesterone and a pharmaceutically acceptable carrier. The oral dosage form can be formulated such that upon single dose administration to a non-pregnant woman in follicular phase, the oral dosage form provides a serum progesterone $C_{24h}$ of at least 0.20 ng/mL. In one embodiment, the oral dosage form can be formulated such that upon single dose administration to a non-pregnant woman in follicular phase, the oral dosage form can provide a serum progesterone $C_{24h}$ of at least 0.30 ng/mL, or at least 0.40 ng/mL. In one embodiment, the oral dosage form can be formulated such that upon single dose administration to a non-pregnant woman in follicular phase, the oral dosage form can provide a serum progesterone $C_{24h}$ of about 0.20 ng/mL to about 5 ng/mL, about 0.20 ng/mL to 3 ng/mL, about 0.20 ng/mL to 2 ng/mL, about 0.5 ng/mL to 3 ng/mL, about 0.50 ng/mL to 2 ng/mL, or about 0.30 ng/mL to 2 ng/mL. In another embodiment, an oral dosage form can be formulated such that upon multiple dose administration reaches a steady state where in serum progesterone $C_{24h}$ of at least 0.35 ng/mL. In another embodiment, serum progesterone $C_{24h}$ of about 0.20 ng/mL or more upon single or multiple dose administration can inhibit ovulation in a female subject.

In another embodiment, an oral dosage form for ongoing administration is provided. The oral dosage form includes an amount of progesterone and a pharmaceutical acceptable release modulator. The oral dosage form can be formulated such that wherein upon release rate testing of the oral dosage using a USP Type-1 dissolution apparatus in 900 mL of de-ionized water with 2.0% (w/v) of sodium lauryl sulfate at 100 rpm, less than 10 wt % of the progesterone is released from the dosage form after about 1 hour, 50 wt % or less of the progesterone is released in the first 6 hours and at least 70 wt % of the progesterone is released within 12 hours.

The oral dosage forms of the present invention can be formulated to provide desirable pharmacokinetic parameters in non-pregnant female subjects. In one embodiment, the oral dosage forms can be formulated such that upon single dose administration to a female subject the oral dosage form provides a serum total pregnane $C_{max}$ of no greater than 40 ng/mL. In one embodiment, the oral dosage form can be formulated such that upon single dose administration to a female subject the oral dosage form can provide a serum total pregnane $C_{max}$ of about 5 ng/mL to 40 ng/mL, about 5 ng/mL to 30 ng/mL, about 5 ng/mL to 20 ng/mL, or about 5 ng/mL to 15 ng/mL. In one embodiment, the oral dosage form can be formulated such that upon single dose administration to a female subject the oral dosage form can provide a serum total pregnane $C_{max}$ of 30 ng/mL or less, 20 g/mL or less, or 10 ng/mL or less. In one embodiment, the oral dosage form can be formulated such that upon single administration to a female subject the oral dosage form can provide a serum total pregnane $C_{max}$ of about 5 ng/mL to 40 ng/mL, about 5 ng/mL to 30 ng/mL, about 5 ng/mL to 20 ng/mL, or about 5 ng/mL to 15 ng/mL.

The oral dosage forms can be formulated such that upon single dose administration to a non-pregnant woman in follicular phase, the oral dosage form provides a serum progesterone $C_{24h}$ of at least 0.20 ng/mL and a serum total pregnane $C_{max}$ of no greater than about 40 ng/mL. In one embodiment, the oral dosage forms can be formulated such that upon single dose administration to a non-pregnant woman in follicular phase, the oral dosage form provides a serum progesterone $C_{24h}$ of at least 0.20 ng/mL and a serum progesterone $C_{max}$ of no greater than about 10 ng/mL. In another embodiment, the oral dosage forms can be formulated such that upon single dose administration to a non-pregnant woman in follicular phase, the oral dosage form provides a serum progesterone $C_{24h}$ of at least 0.20 ng/mL, but less than or equal to about 1.5 ng/mL. In a further embodiment, the oral dosage forms can be formulated such that upon single dose administration to a non-pregnant woman in follicular phase, the oral dosage form provides a serum progesterone $C_{24h}$ of at least 0.20 ng/mL and a serum allopregnanolone $C_{max}$ of no greater than about 10 ng/mL. In still a further embodiment, the oral dosage forms can be formulated such that upon single dose administration to a non-pregnant woman in follicular phase, the oral dosage form provides a serum progesterone $C_{24h}$ of at least 0.20 ng/mL when the dosage form includes progesterone in an amount of about 200 mg to about 600 mg, and in a specific embodiment, 400 mg.

In another embodiment, the oral dosage forms can be formulated such that upon single dose administration to a female subject the oral dosage form provides a serum progesterone $C_{max}$ of no greater than 10 ng/mL. In another embodiment, the oral dosage forms can be formulated such that upon single dose administration to a female subject the oral dosage form provides a serum progesterone $C_{max}$ of about 8 ng/mL or less, about 7 ng/mL or less, about 6 ng/mL or less, or about 5 ng/mL or less.

In still a further embodiment, the oral dosage forms can be formulated such that upon single dose administration to a female subject the oral dosage form provides a serum progesterone $C_{24h}$ of 1.5 ng/mL or less. In a further embodiment, the oral dosage forms can be formulated such that upon single dose administration to a female subject the oral dosage form provides a ratio of serum progesterone $C_{max}$ to $C_{24h}$ that is about 1:1 and about 10:1. The oral dosage forms can also be formulated such that upon single dose administration to a female subject the oral dosage form can provide a serum allopregnanolone $C_{max}$ of no greater than 10 ng/mL. In one embodiment, the oral dosage forms can be formulated such that upon single dose administration to a female subject the oral dosage form can provide a serum allogregnalone $C_{max}$ of about 2 ng/mL to 10 ng/mL, about 2 ng/mL to 8 ng/mL, about 2 ng/mL to 6 ng/mL, or from about 1 ng/mL to 5 ng/mL. The oral dosage forms can also be formulated such that upon single dose administration to a female subject the oral dosage form can provide a serum allopregnanolone $C_{max}$ of no greater than about 8 ng/mL or less, about 7 ng/mL or less, about 6 ng/mL or less, or about 4 ng/mL or less. In one embodiment the oral dosage forms can also be formulated such that upon single dose administration to a female subject, the oral dosage form can provide a serum allopregnanolone $C_{max}$ of about 2 to 10 ng/mL, about 2 to 8 ng/mL; about 2 to 6 ng/mL; or about 1 to 5 ng/mL.

In a further embodiment, the oral dosage form can, upon single dose administration to a female subject, provide a ratio of serum allopregnanolone $C_{max}$ to serum progesterone $C_{24h}$ of not more than 50:1. In an additional embodiment, the oral dosage form can, upon single dose administration to a female subject in follicular phase, provide a ratio of serum allopregnanolone $C_{max}$ to serum progesterone $C_{24h}$ of about 7.8:1 to about 1:1.

Upon single dose administration to a female subject, the oral dosage form can provide an allopregnanolone serum $C_{ave(0-24)}$ of at least about 0.5 ng/mL. In another embodiment, the upon single dose administration to a female subject, the oral dosage form can provide an allopregnanolone serum $C_{ave(0-24)}$ of about 0.5 ng/mL to about 10 ng/mL, with the allopregnanolone $C_{ave(0-24)}$ being measured using the conventional radio immune assay method. Still further, in one embodiment, the oral dosage form can, upon single dose administration to a female subject, provide a serum progesterone $C_{36h}$ of not less than 0.20 ng/mL. Still further, in another embodiment, the oral dosage form can provide to a female subject, a steady state serum progesterone $C_{36h}$ of not less than 0.20 ng/mL.

In another embodiment, upon single dose administration to a female subject the oral dosage form can provide a serum progesterone $AUC_{12-24h}$ (ng*h/mL) to administered progesterone dose (mg) ratio of at least 0.005 (ng*h/ml)/mg. In still a further embodiment, upon single dose administration to a female subject, the oral dosage form can provide a ratio of administered progesterone dose (mg) to serum progesterone $C_{24h}$ (ng/mL) of about 100 mg/(ng/ml) to about 1000 (ng/ml)/mg. In another embodiment, upon single dose administration to a female subject, the oral dosage form can provide a ratio of administered progesterone dose (mg) to serum progesterone $C_{36h}$ (ng/mL) of about 100 mg/(ng/ml) to about 1000 (ng/ml)/mg. In another embodiment, upon single dose administration to a female subject, the oral dosage form can provide a ratio of administered progesterone dose (mg) to serum total pregnane $C_{max}$ (ng/mL) of at least 20 (ng/ml)/mg. In another embodiment, upon single dose administration to a female subject, the oral dosage form can provide a ratio of administered progesterone dose (mg) to serum allopregnanolone $C_{max}$ of at least 50 mg/(ng/mL).

The oral dosage forms can also provide other pharmacokinetic parameters such as, upon single dose administration to a female subject, the oral dosage form can provide a progesterone $C_{ave(12-24)}$ of at least about 0.11 ng/mL. In one embodiment, the oral dosage form can be such that upon single dose administration to a subject the oral dosage form provides a progesterone $AUC_{12-24}$ of at least 3 ng*h/mL. In another embodiment, upon single dose administration to a female subject the oral dosage form can provide an allopregnanolone $C_{max}$ of not more than about 10 ng/mL. In another embodiment, upon single dose administration to a female subject the oral dosage form can provide a progesterone $C_{24h}$ of at least about 0.2 ng/mL. In another embodiment, upon single dose administration to a female subject the oral dosage form can provide a serum progesterone $C_{36h}$ of not less than about 0.20 ng/mL. In another embodiment, upon single dose administration of the progesterone-containing oral dosage form to a female subject, the progesterone-containing oral dosage form can provide a ratio of serum progesterone $C_{24h}$ to progesterone dose administered (mg) of at least about $3.33 \times 10^{-4}$ (ng/ml)/mg. In another embodiment, upon single dose administration of the progesterone-containing oral dosage form to a female, the progesterone-containing oral dosage form can provide a ratio of serum progesterone $C_{36h}$ (ng/mL) to progesterone dose administered (mg) of at least about $3.33 \times 10^{-4}$ (ng/ml)/mg. In still another embodiment, upon single dose administration of one of the progesterone-containing oral dosage forms to a female, the progesterone-containing oral dosage form can provide a an all allopregnanolone serum $C_{ave(0-24)}$ of at least 0.3 ng/mL.

The oral dosage forms of the present disclosure can be formulated to have progesterone release rates that are effective in achieving desirable delivery parameters. In one embodiment, the oral dosage form can have an in vitro release rate such that, when measured using a USP Type-1 dissolution apparatus in 900 mL of de-ionized water with 2.0% (w/v) of sodium lauryl sulfate at 100 rpm, about 10 wt % or less of the progesterone in the oral dosage form is released in the first 60 minutes and at least 70 wt % of the progesterone is released from the oral dosage form within 12 hours. In one embodiment, the oral dosage form can be formulated such that upon in vitro dissolution using the above parameters the oral dosage form releases less than 25 wt % of progesterone in the first three hours. In another embodiment, the oral dosage form can be formulated to release substantially all of the progesterone within the about 22 hours.

The oral dosage forms of the present disclosure can be formulated to include from about 100 mg to about 600 mg of progesterone. In another embodiment, the oral dosage form can include about 200 mg to about 600 mg of progesterone. In yet a further embodiment, the oral dosage form can include about 300 mg to about 500 mg. In yet another embodiment, the oral dosage form can include about 200 to about 400 mg. In a further embodiment, the oral dosage form can include 400 mg progesterone. In a further embodiment, the oral dosage form can include 200 mg progesterone. The progesterone can comprise from 15 wt % to about 45 wt % of the oral dosage form. In one embodiment, the progesterone can comprises from about 15 wt % to about 45 wt % of the oral dosage form. The progesterone can be present in any form known in the art. As needed, in the compositions and forms of the present invention, the progesterone can be micronized, nano-sized, and/or in amorphous forms. In one embodiment, the progesterone can be present or added to the oral dosage form in an untreated form such as unmicronized, unmilled and/or unsieved forms. In another embodiment, the oral dosage form can include a combination of these forms. In another embodiment, the progesterone can be present or added to the oral dosage form as treated form such as micronized, nano-sized, milled or sieved forms, or combinations thereof. The progesterone can be solubilized in one or more of the other components of the oral dosage form, such as the carrier, or it can be suspended within the oral dosage form. The suspended portion of progesterone may be partially or completely in unmicronized, milled, sieved, or amorphous forms or combinations thereof.

The progesterone in the oral dosage forms of the present invention can be partially or fully in the form of a high-energy solid which increases the release rate in an aqueous medium significantly compared to at least one of its unmilled or unmicronized crystalline forms (low energy forms). Examples of high-energy forms include amorphous forms and the like. In one embodiment the high-energy form progesterone of present invention may be physico-chemically pure. In yet another embodiment the high-energy form progesterone can be physically and/or chemically associated with at least one additional substance, such as for example alcohol, pyrrolidone, cellulose, polyol, polyethylene glycol, dextrins, cyclodextrins and the like. Several methods known in the art may be used to produce the high-energy form progesterone of the present invention, for example co-precipitation, solid-solution, co-melting, co-grinding, spray drying with co-solvent, controlled precipitation from super-saturated solutions, solidified supersaturated solutions, and combinations thereof.

In some embodiments, the oral dosage forms of the present invention can be formulated to include an estrogenic agent. Non-limiting examples of estrogenic agents that can be included in the oral dosage forms include estradiol, conjugated estradiol, conjugated equine estrogens, esterified estradiol, and combinations thereof. In one embodiment, the estrogenic agent can be estradiol, ethinyl estradiol, estradiol valerate, or combinations thereof. The estrogenic agent can be a bio-identical estrogenic agent. The estrogenic agent can present in the oral dosage form in an amount of 0.001 mg to about 7.5 mg. In another embodiment, the estrogenic agent can be ethinyl estradiol and can be present in the oral dosage form in an amount of about 0.01 mg to about 0.05 mg. In a specific embodiment, the ethinyl estradiol can be present in the oral dosage form in an amount of about 0.01 mg to about 0.1 mg. In another specific embodiment, ethinyl estradiol amount is about 0.030 mg in the dosage form. In another embodiment, the estrogenic agent can be estradiol valerate and can be present in the oral dosage form in an amount of about 0.75 mg to about 7.5 mg. In a specific embodiment, the estrogenic agent can be estradiol valerate and can be present in the oral dosage form in an amount of about 1.5 mg to about 5.5 mg. In another embodiment, the estrogenic agent can be estradiol and can be present in the oral dosage form in an amount of 0.5 mg to about 5 mg. In a specific embodiment, the estrogenic agent can be estradiol and the estradiol can be present in the oral dosage form in an amount of 1 mg to about 5 mg. In another specific embodiment, the estrogenic agent can be estradiol and the estradiol can be present in the oral dosage form in an amount of 1 mg to about 3.5 mg. The estrogenic agent can be present in the oral dosage form in an amount such that the ratio (w/w) of the amount of estrogenic agent to the amount of progesterone in the oral dosage form is about $3 \times 10^{-5}:1$ to about $3 \times 10^{-2}:1$.

The oral dosage forms of the present disclosure can include one or more pharmaceutically acceptable carrier. The pharmaceutically carrier can be selected from a wide range of compounds and classes of compounds. The pharmaceutically acceptable carrier can comprise from 55 wt % to about 85 wt % of the oral dosage form. In one embodiment, the pharmaceutically acceptable carrier can comprise about 67 wt % to 82 wt % of the oral dosage form. In one embodiment, the pharmaceutically acceptable carrier can comprise about 50 wt % to 75 wt % of the oral dosage form.

Non-limiting examples of compounds that can be used as at least a part of the pharmaceutically acceptable carrier include without limitation celluloses; dextrins, gums, carbomers, methacrylates, sugars, lactoses, inorganic carbonates, oxides, chlorides, sulphates and the like; salts of calcium; salts of magnesium; salts of fatty acids; inorganic and organic acids, bases and salts; propylene glycol; glycerols; fatty acids; fatty alcohols; fatty acid esters; glycerol esters; mono-, di- or triglycerides; edible oils; omega oils; vegetable oils, hydrogenated vegetable oils; partially or fully hydrogenated vegetable oils; glycerol esters of fatty acids; waxes; alcohols; gelatin; polyethylene glycol; polyethylene oxide co-polymers; silicates; antioxidants, tocopherols, sugar stearates, starches, shellac, resins, proteins, acrylates; methyl copolymers; polyvinyl alcohol; starch; phthalates; and combinations thereof.

In one embodiment, the carrier can include at least one component selected from celluloses, dextrins, gums, carbomers, methacrylates, inorganic carbonates, salts of calcium, salts of magnesium, fatty acids, fatty acid esters, gelatin, lactoses, polyethylene glycol, polyethylene oxide co-polymers, silicates, partially hydrogenated vegetable oils, fully hydrogenated vegetable oils, waxes, antioxidants, tocopherol, sugar stearates, starches, shellac, resins, proteins, and combinations thereof.

In another embodiment, the carrier can include at least one component selected from celluloses, dextrins, gums, carbomers, methacrylates, sugars, lactoses, inorganic carbonates, salts of calcium, salts of magnesium, salts of fatty acids, inorganic and organic acids, bases and salts, propylene glycol, glycerols, fatty acids, fatty alcohols, fatty acid esters, glycerol esters, mono-glycerol esters of fatty acids, di-glycerol esters of fatty acids, mixtures of mono-glycerol and di-glycerol esters of fatty acids, omega oils, waxes, alcohols, gelatin, polyethylene glycol, polyethylene oxide co-polymers, silicates, antioxidants, tocopherol, sugar stearates, starches, shellac, resins, proteins, acrylates, methyl copolymers, polyvinyl alcohol, starch, phthalates, and combinations thereof.

It is important to note that carrier compositions used in the present invention may serve multiple functional purposes within the oral dosage form. For example, a carrier may also function as a disintegrant or release modulator. In one aspect, the pharmaceutically acceptable carrier can include a release modulator. The release modulator can comprise about 8 wt % to about 80 wt % of the oral dosage form. In another embodiment, the release modulator can comprise about 20 wt % to about 80 wt % of the oral dosage form. In one embodiment, the release modulator can comprise about 25 wt % to about 80 wt %, 30 wt % to about 70 wt %, 35 wt % to about 70 wt %, 40 wt % to about 65 wt %, about 40 wt % to about 60 wt %, about 5 wt % to about 35 wt %, or about 8 wt % to about 20 wt %, each based on entire oral dosage form.

In one embodiment, the release modulator can be present in an amount such that the ratio of the release modulator to the amount of progesterone is from about 0.75:1 to about 4:1. In another embodiment, the ratio of release modulator to the amount of progesterone can be from about 1.3:1 to about 3:1. In another specific embodiment, the ratio of release modulator to the amount of progesterone can be from about 1:1 to about 2:1. In another specific embodiment, the ratio of release modulator to the amount of progesterone can be from about 1:1, about 1.5:1, about 2:1 or about 3:1.

In one embodiment, the release modulator can be selected from compounds such as celluloses; gums; xanthan gum; polyethylene glycol, particularly high molecular weight; polyethylene oxide co-polymers; 2,3-dihydroxypropyl methacrylate (DHPMA)and 2-hydroxyethyl methacrylate (HEMA); chitosan; dextrins; sugars and sugar esters; carbomers; polyvinyl pyrrolidones; starches; croscarmelloses; block copolymers, graft copolymers of lactic acid, glycolic acid, epsilon-caprolactone, lactic-co-glycolic acid oligomers, trimethylene carbonate, anhydrides, amino acids acrylates; lipophilic resins; ethyl cellulose (EC), methylethyl cellulose (MEC), carboxymethyl ethylcellulose (CMEC), hydroxyethyl cellulose (HEC), cellulose acetate (CA), cellulose propionate (CPr), cellulose butyrate (CB), cellulose acetate butyrate (CAB), cellulose acetate phthalate (CAP), cellulose acetate trimellitate (CAT), hydroxypropylethyl cellulose phthalate (HPMCP), hydroxypropyl methyl cellulose acetate succinate (HPMCAS), hydroxypropyl methyl cellulose acetate trimellitate (HPMCAT), ion-exchange resin; poloxamers; and ethylhydroxy ethylcellulose (EHEC) tocopherol; shellac; fatty acids; mono-, di-, tri-esters of fatty acids with glycerol; sucrose esters with fatty acids; cetyl alcohol; stearic acid; glyceryl monosterate; glyceryl distearate; glyceryl tristearate; glyceryl palmitostearate; hydrogenated castor oil; butyl and glycol esters of fatty acids; oleic acid; cetyl alcohol; stearyl alcohol; cetostearyl alcohol; hydrogenated vegetable oil; waxes; bees wax; lard; omega fatty acid esters; hydrogenated soybean oil; hydrogenated vegetable oil; hydrogenated cottonseed and castor oil; partially hydrogenated soybean oil; partially hydrogenated castor oil; partially soy and cottonseed oil; phospholipids; hydrogenated oils, and their derivatives and combinations thereof. The above list should not be construed as being limiting to the types and number of compounds that can be used as release modulators.

In one embodiment, the release modulator can be selected from compounds such as celluloses, gums, carbomers, methacrylates, polyethylene glycol, polyethylene oxide co-polymers, acrylates, methyl copolymers, polyvinyl alcohol, povidones, phthalates, fatty acids, hydrogenated vegetable oils, and mixtures thereof Non-limiting additional examples of release modulators that can be included as the carrier or a component of the carrier can include: polyethylene glycols having a weight average molecular weight of about 1000 and more, carbomer, methyl methacrylate copolymers, methacrylate copolyers, hydroxypropyl methyl cellulose, hydroxypropyl cellulose, cellulose acetate phthalate, ethyl cellulose, methyl cellulose and their derivatives, ion-exchange resin, mono- di- tri-esters of fatty acids with glycerol and mixtures thereof, tocopherol and its esters, sucrose esters with fatty acids, polyvinyl pyrollidone, xanthan gums, cetyl alcohol, waxes, fats and oils, proteins, alginate, polyvinyl polymers, gelatins, organic acids, and their derivatives and combinations thereof. In one embodiment, the release modulator can be selected from compounds such as methyl celluloses, carboxymethyl celluloses, ethyl celluloses, hydroxypropyl celluloses, hydroxypropyl methyl celluloses, croscarmelloses, carbomers, polyvinyl pyrrolidones, gums, stearic acid, glyceryl stearates, sugar stearates, gelatins, polyethylene glycols having a weight average molecular weight of about 100 or more, methyl methacrylate co-polymers, cellulose acetates, cellulose acetate phthalates, and mixtures thereof.

In one embodiment, the release modulator can include a cellulose, and the cellulose can be selected from such compounds as methyl cellulose, carboxymethyl cellulose, ethyl cellulose, hydroxypropyl cellulose, hydroxypropyl methyl cellulose, and mixtures thereof. Other celluloses or cellulosics that can be used include microcrystalline cellulose, ethyl cellulose (EC), carboxymethyl ethylcellulose (CMEC), hydroxyethyl cellulose (HEC), cellulose acetate (CA), cellulose propionate (CPr), cellulose butyrate (CB), cellulose acetate butyrate (CAB), cellulose acetate phthalate (CAP), cellulose acetate trimellitate (CAT), hydroxypropyl methyl cellulose phthalate (HPMCP), hydroxypropyl methyl cellulose acetate succinate (HPMCAS), hydroxypropyl methyl cellulose acetate trimellitate (HPMCAT), and ethylhydroxy ethylcellulose (EHEC). A particularly preferred class of such cellulosics comprises various grades of low viscosity (MW less than or equal to 50,000 daltons) and high viscosity (MW greater than 50,000 daltons) HPMC. Commercially available low viscosity HPMC polymers include the Dow METHOCEL® series E5, E15LV, E50LV and K100LY, while high viscosity HPMC polymers include E4MCR, E10MCR, K4M, K15M and K100M; especially preferred in this group are the METHOCEL® K series. Other commercially available types of HPMC include the Shin Etsu METOLOSE® 90SH series.

In one embodiment, when the release modulator is a cellulose, the ratio (w/w) of the amount release modulator to the amount of the progesterone in the oral dosage form can be from about 0.75:1 to about 4:1. In another embodiment, when the release modulator can be a cellulose, and the ratio (w/w) of the amount release modulator to the amount of the progesterone in the oral dosage form can be from about 1.3:1 to about 2.7:1. In another specific embodiment, the ratio (w/w) can be from about 1:1. In yet a further specific embodiment, the ratio of release modulator to the amount of progesterone (w/w) can be about 1.5:1, about 1.8:1, about 2:1, or about 2.25:1.

In one embodiment, the release modulator can be a hydrophilic release modulator. When present, the hydrophilic release modulator can comprise all or a portion of the release modulator. In one embodiment, the hydrophilic release modulator can be present in an amount of about 10 wt % to about 65 wt % of the dosage form. Non-limiting examples of hydrophilic release modulators include celluloses; gums; xanthan gum; polyethylene glycol, particularly high molecular weight; polyethylene oxide co-polymers; 2,3-dihydroxypropyl methacrylate (DHPMA)and 2-hydroxyethyl methacrylate (HEMA); chitosan; dextrins; sugars and sugar esters; carbomers; polyvinyl pyrrolidones; starches; croscarmelloses; block copolymers, graft copolymers of lactic acid, glycolic acid, epsilon-caprolactone, lactic-co-glycolic acid oligomers, trimethylene carbonate, anhydrides, and amino acids acrylates. Non-limiting examples of hydrophilic celluloses or hydrophilic cellulosics that can used include carboxymethyl cellulose (CMC), hydroxypropyl cellulose (HPC), hydroxypropyl methyl cellulose (HPMC), hydroxypropyl methyl cellulose acetate succinate (HPMCAS). A particularly preferred class of such cellulosics comprises various grades of low viscosity (MW less than or equal to 50,000 daltons) and high viscosity (MW greater than 50,000 daltons) HPMC. Commercially available low viscosity HPMC polymers include the Dow METHOCEL® series E5, E15LV, E50LV and K100LY, while high viscosity HPMC polymers include E4MCR, E10MCR, K4M, K15M and K100M; especially preferred in this group are the METHO- CEL® K series. Other commercially available types of HPMC include the Shin Etsu METOLOSE® 90SH series.

Lipophilic release modulators may also be used. The lipophilic release modulator can be either a non-lipid lipophilic release modulator or a lipidic lipophilic release modulator. When present, the amount of lipophilic release modulator can vary depending on various factors. In one embodiment, the lipophilic release modulator can comprise about 8 wt % to about 50 wt % of the oral dosage form. In another embodiment, the lipophilic release modulator can comprise about 5 wt % to about 30 wt %, 8 wt % to 20 wt %, or 20 wt % to about 50 wt %, each based on the total oral dosage form. In another embodiment, the lipophilic release modulator can be a non-lipidic lipophilic release modulator and can be present at about 8 wt % to about 35 wt % of the oral dosage form. In another embodiment, the lipophilic release modulator can be a lipidic release modulator and can be present at about 10 wt % to about 50 wt % of the oral dosage form.

Non-limiting examples of non-lipidic lipophilic release modulators that can be used include lipophilic resins; ethyl cellulose (EC), methylethyl cellulose (MEC), carboxymethyl ethylcellulose (CMEC), hydroxyethyl cellulose (HEC), cellulose acetate (CA), cellulose propionate (CPr), cellulose butyrate (CB), cellulose acetate butyrate (CAB), cellulose acetate phthalate (CAP), cellulose acetate trimellitate (CAT), hydroxypropyl methyl cellulose phthalate (HPMCP), hydroxypropyl methyl cellulose acetate succinate (HPMCAS), hydroxypropyl methyl cellulose acetate trimellitate (HPMCAT), ion-exchange resin; poloxamers; and ethylhydroxy ethylcellulose (EHEC) tocopherol; shellac; and combinations thereof. Non-limiting examples of lipidic lipophilic release modulators include fatty acids; mono-, di-, tri-esters of fatty acids with glycerol; sucrose esters with fatty acids; cetyl alcohol; stearic acid; glyceryl monosterate; glyceryl distearate; glyceryl tristearate; glyceryl palmitostearate; hydrogenated castor oil; butyl and glycol esters of fatty acids; oleic acid; cetyl alcohol; stearyl alcohol; cetostearyl alcohol; hydrogenated vegetable oil; waxes; bees wax; lard; omega fatty acid esters; hydrogenated soybean oil; hydrogenated vegetable oil; hydrogenated cottonseed and castor oil; partially hydrogenated soybean oil; partially hydrogenated castor oil; partially soy and cottonseed oil; phospholipids; hydrogenated oils, and their derivatives and combinations thereof.

In one embodiment, the pharmaceutically acceptable carrier can optionally include at least one surfactant. When present, the surfactant can comprise about 0.1 wt % to about 25 wt % of the oral dosage form. In one embodiment, the surfactant can comprise about 4 wt % to about 10 wt % of the oral dosage form. In one embodiment, the surfactant can be a hydrophilic surfactant. A hydrophilic surfactant has a surface active property and that has an HLB value of 10 or more. In one embodiment, the hydrophilic surfactant can be selected and present in an amount such that the hydrophilic surfactant solubilizes less than 10 wt % of the progesterone in the oral dosage form. The hydrophilic surfactants can be an anionic or non-ionic surfactant. Non-limiting examples of hydrophilic surfactants that can be included in the oral dosage forms include sodium lauryl sulphate, polysorbate 80, sodium docusate, polyoxyl castor oils, polyoxyl hydrogenated castor oils etc., and mixtures thereof. In another embodiment, the hydrophilic surfactant can be present in an amount such that the ratio (w/w) of the total amount of the hydrophilic surfactant to the amount of progesterone in the dosage form is about 1:10 to about 1:2. In another embodiment, the ratio (w/w) of the total amount of the hydrophilic surfactant to the amount of progesterone in the dosage form can be from about 1:9 to about 1:2, about 1:8 to about 1:2, about 1:7 to about 1:4, or about 1:6 to about 1:4. In another embodiment, the hydrophilic surfactant can be present in an amount such that the ratio (w/w) of the total amount of the hydrophilic surfactant to the amount of total release modulator in the dosage form is from about 1:5 to about 1:15 or about 1:5 to about 1:10. In a particular embodiment, the progesterone containing oral dosage form can include progesterone, a release modulator agent, and optionally a hydrophilic surfactant. The progesterone can be present in an amount from about 10 wt % to 40 wt % of the dosage form and the total hydrophilic surfactant, when present, can comprise about 4 wt % to 10 wt % of the oral dosage form. The oral dosage form can be formulated to have a ratio (w/w) of release modulator to the amount of progesterone in the dosage form of about 1:1 to 3:1.

In another embodiment, progesterone containing oral dosage forms can include progesterone, a release modulator agent, and optionally a hydrophilic surfactant. The progesterone can be present in an amount of about 20 wt % to 40 wt % of the dosage form. The ratio of the amount of the release modulator to the amount of the progesterone amount in the dosage form can be about 1.3:1 to 2.3:1 and the optional surfactant does not exceed 10 wt % of the dosage form. In another embodiment, the progesterone-containing oral dosage form can include progesterone, a release modulator agent and a hydrophilic surfactant. The progesterone can be present in an amount of about 20 wt % to 40 wt % of the oral dosage form. The total hydrophilic surfactant can be present in an amount of about 4 wt % to 8 wt % of the oral dosage form and the ratio (w/w) of the amount of the release modulator to the amount of progesterone in the oral dosage form can be about 1.3:1 to 2.3:1.

In one embodiment, the oral dosage form can be substantially free of edible oils. In another embodiment, the oral dosage form can be substantially free of oils having a carbon chain length of 12 to 18 carbons. In another embodiment, the oral dosage form can be substantially free of hydrophilic surfactants. The oral dosage form can also include one or more pharmaceutical aids and excipients to improve performance, handling, or processing. Non-limiting examples include antioxidants, binders, buffers, diluent, disintegrant, adsorbents, fillers, flavors, lactoses, inorganic carbonates, oxides, chlorides and sulphates, salts of sodium, calcium and magnesium, dextrins, salts of fatty acids, inorganic and organic acids and bases, propylene glycol, glycerols, fatty acids, fatty acid esters, glycerol esters, monoglyceride, diglycerides, or triglycerides, edible oils, omega oils, vegetable oils, fatty alcohols, waxes, alcohols, gelatin, silicates, tocopherols, sugars, sugar stearates, starches, shellac, resins, proteins, polyvinyl alcohol, and combinations thereof. The oral dosage form can further include release-rate enhancers such as, for example, wetting agents, surfactants, pH modifiers, matrix materials, complexing agents, solubilizers, pigments, lubricants, glidants, and the like. In one embodiment the compositions comprise at least one wetting agent and/or surfactant selected from the group comprising hydrophilic, lipophilic, amphiphilic, ionic, nonionic surfactants. In another embodiment, the composition can be substantially free of added hydrophilic surfactants.

In one embodiment of the present invention, the oral dosage form can optionally include edible oils in an amount not exceeding about 10 wt % of the dosage form. In a specific embodiment, the amount of edible oil does not exceed 5 wt % of the dosage form.

In one embodiment of the present invention, the oral dosage form can optionally include oils containing omega fatty acids. Non-limiting examples of oils containing omega fatty acids, can include, but are not limited to, linoleic acid (ALA), eicosapentaenoic acid (EPA), and docosahexaenoic acid (DHA), all of which are polyunsaturated with carbon chain length greater than 20. In another embodiment omega-3 fatty acids can be administered with progesterone concomitantly or sequentially. The oral dosage forms of the present invention can include a pharmaceutically acceptable carrier. The carrier can be a single ingredient, or a mixture of ingredients. Additionally, the carrier can take the form of an encapsulation coat, an absorbing agent, a coating substance, a controlled release device, a release modifying or release controlling agent, surfactants, or a combination thereof. In one embodiment, the carrier can be admixed with the progesterone. In another embodiment, the carrier can adsorb, entrap, or encapsulate at least a portion of the progesterone. In yet another embodiment, the carrier can act to solubilize the progesterone.

Non-limiting examples of fillers, or diluents include celluloses such as those other than used to modify drug release rates from the composition and/or dosage forms, lactose, mannitol, xylitol, dibasic calcium phosphate (anhydrous and dihydrate) and starch. Non-limiting examples of disintegrants include sodium starch glycolate, sodium alginate, carboxy methyl cellulose sodium, and croscarmellose sodium, and crosslinked forms of polyvinyl pyrrolidone such as those sold under the trade name Crospovidone (available from BASF Corporation). Non-limiting examples of binders can include methyl cellulose, microcrystalline cellulose, starch, and gums such as guar gum, and tragacanth. Non-limiting examples of lubricants can include magnesium stearate, calcium stearate, and stearic acid. Non-limiting examples of preservatives can include sulfites (an antioxidant), benzalkonium chloride, methyl paraben, propyl paraben, benzyl alcohol and sodium benzoate.

In another embodiment, the oral dosage form of this invention can optionally include polyethylene glycol (PEG) having a molecular weight of about 400 to about 20,000, or mixtures of such polyethylene glycols. When included in an oral dosage form, the amount of PEG can make up less than 30 wt % of the oral dosage form. In one embodiment, the amount of PEG can be about 5 wt % to about 30 wt %, about 5 wt % to about 25 wt %, about 5 wt % to about 20 wt %, about 5 wt % to about 15 wt %, or about 5 wt % to about 10 wt %. In a specific embodiment, the amount of PEG can make up about 10 wt % or less or about 5 wt % or less, of the oral dosage form.

Non-limiting examples of suspending agents or thickeners can include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide. Non-limiting examples of anti-caking agents or fillers include silicon oxide and lactose. Non-limiting examples of solubilizers can include ethanol, propylene glycol or polyethylene glycol.

The addition of pH modifiers such as acids, bases, or buffers may be beneficial, retarding the release of progesterone (e.g., bases such as sodium acetate or amines) or, alternatively, enhancing the rate of release of progesterone (e.g., acids such as citric acid or succinic acid). Other conventional excipients may also be employed in the oral dosage forms of this invention, including those well-known in the art. Generally, excipients such as pigments, lubricants, flavorants, and so forth may be used for customary purposes and in typical amounts without adversely affecting the properties of the compositions.

The dosage form(s) are not limited with respect to size, shape or general configuration, and may be formulated into a variety of dosage forms including, but not limited to two piece hard gelatin capsules, soft gelatin capsules, beads, beadlets, granules, spherules, pellets, microcapsules, microspheres, nanospheres, nanocapsules, tablets, or combinations thereof. Other oral dosage forms known to those of ordinary skill in the art may also be used. In one aspect, the oral dosage form may be a capsule or tablet. In one embodiment, the oral dosage form can be a matrix tablet.

The progesterone of the oral dosage forms of the present invention may be incorporated into an osmotic sustained or controlled or delayed release dosage form. Such dosage forms have at least two components: (a) the core which contains an osmotic agent and progesterone; and (b) a water permeable, non-dissolving and non-eroding coating surrounding the core, the coating controlling the influx of water to the core from an aqueous environment of use so as to cause drug release by extrusion of some or all of the core to the environment of use. The osmotic agent contained in the core of this dosage form may be an aqueous-swellable hydrophilic polymer or it may be an osmogen, also known as an osmagent. The coating can be polymeric, aqueous-permeable, and can have at least one delivery port that is pre-formed or formed in situ. Examples of such dosage forms are well known in the art. See, for example, Remington: The Science and Practice of Pharmacy, 20.sup.th Edition, 2000.

The oral dosage forms of the present invention can include a coating. In one embodiment, the coating can include all or a portion of the release modulator. One class of preferred coating materials are the pharmaceutically acceptable methacrylic acid copolymers, which are anionic in character, based on methacrylic acid and methyl methacrylate, for example having a ratio of free carboxyl groups:methyl esterified carboxyl groups of 1:<3, e.g. around 1:1 or 1:2, and with a mean molecular weight of 135000. Some of these polymers are known and sold as enteric polymers, for example having a solubility in aqueous media at pH 5.5 and above, such as the commercially available EUDRAGIT enteric polymers, such as Eudragit L 30, a cationic polymer synthesized from dimethylaminoethyl methacrylate, Eudragit S and Eudragit NE. The coating may include conventional plasticizers, including dibutyl phthalate, dibutyl sebacate, diethyl phthalate, dimethyl phthalate, triethyl citrate, benzyl benzoate, butyl and glycol esters of fatty acids, mineral oil, oleic acid, stearic acid, cetyl alcohol, stearyl alcohol, castor oil, corn oil, coconut oil, and camphor oil, and other excipients such as anti-tack agents, glidants, etc. For plasticizers, triethyl citrate, coconut oil and dibutyl sebacate are also useful. Typically the coating may include from about 0.1 to about 25 wt % plasticizer and from about 0.1 wt % to about 10 wt % anti-tack agents. The enteric coating may also include insoluble materials, such as shellac, alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin, 1,2-, 3,4-diepoxybutane, etc. The enteric coating may also include starch and/or dextrin. The coating, including enteric coatings, may be applied to the oral dosage form by dissolving or suspending the enteric coating materials in a suitable solvent. Examples of solvents suitable for use in applying a coating include alcohols, such as methanol, ethanol, isomers of propanol and isomers of butanol, ketones, such as acetone, methylethyl ketone and methyl isobutyl ketone, hydrocarbons, such as pentane, hexane, heptane, cyclohexane, methylcyclohexane, and octane; ethers, such as methyl tert-butyl ether, ethyl ether and ethylene glycol monoethyl ether; chlorocarbons, such as chloroform, methylene dichloride and ethylene dichloride; tetrahydrofuran; dimethylsulfoxide; N-methylpyrrolidinone; acetonitrile; water; and mixtures thereof.

Coating may be conducted by conventional techniques, such as by pan coaters, rotary granulators and fluidized bed coaters such as top-spray, tangential-spray or bottom-spray (Wurster coating), most preferably the latter. One preferred coating solution consists of about 40 wt % Eudragit L30-D55 and 2.5 wt % triethylcitrate in about 57.5 wt % water. This enteric coating solution may be coated onto the core of the oral dosage form using a pan coater. The enteric coating materials listed above can be used to granulate a progesterone containing mixture. The resultant granulate may be filled into capsules or compressed to form tablets or caplets. The release of progesterone from the oral dosage forms or components of the dosage form (e.g. granules), of the present disclosure can be controlled or delayed. The oral dosage forms of the present invention can be formulated for once-a-day or twice daily (i.e. once every 12 hours) administration of progesterone.

The oral dosage form disclosed herein can be formulated for administration once every 24 hours. In particular, the oral dosage forms can be formulated for administration once every 24 hours as part of a dosing regimen that provides contraception. In one embodiment, the oral dosage forms can be formulated for administration once every 12 hours. The oral dosage forms can be formulated to provide contraception to a non-pregnant woman. In another embodiment, the oral dosage forms can be formulated for administration to a woman for a non-contraceptive indication. Non-limiting examples of non-contraceptive uses for which the oral dosage forms may be utilized include treatment of conditions such as endometriosis, irregular menstrual cycles, acne, dysmenorrhea and premenstrual symptoms, dysphoric disorder, polycystic ovarian syndrome (PCOS), perimenopause, hirsutism, and combinations thereof. In one aspect of the invention the oral dosage form can be formulated to provide contraception to a non-pregnant female subject when administered daily from day-1 to at least day-21 of a 28 day menstrual cycle in a normal cyclic woman.

Unless otherwise specified, the oral dosage forms of the present invention can be administered to a subject with a meal or a snack. The dosage form can be administered within about 30 minutes of the start of the meal/snack. The administration is generally expected to be at the same time, or about the same time every day. In one embodiment, the meal or snack can provide about 200 calories to about 1000 calories. In another embodiment, the oral dosage form can be administered with a standard meal. In another embodiment, the oral dosage form can be administered with a meal that provides about 20%-50% of the calories from fat. In another embodiment, the oral dosage form can be administered with a high-fat, high calorie meal/snack. In another embodiment, the oral dosage form can be administered with a meal/snack that provides about 500 calories to about 1000 calories. In another embodiment, the oral dosage form can be administered with a meal that provides about 400 calories to about 700 calories which are derived from fat. The compositional make-up of the meals/snack administered can vary depending on the tastes and dietary needs of the subject. In some situations it may be beneficial to administer the oral dosage forms with a meal/snack that provides amounts of fat of 0 grams up to about 50 grams. In one embodiment, the meal/snack can provide about 10 g to about 50 g of fat. In yet a further embodiment, the meal can provide about 20 g to about 30 g of fat. It should be noted that dosage forms of the current invention can be administered to a subject under fasting condition. Accordingly, the daily dosage regimen can be adjusted to provide the serum progesterone $C_{24h}$ concentration of about 0.20 ng/dL or higher.

The present invention also provides for kits used in disbursement and administration of the oral dosage forms of the present invention. The kit can include a plurality of doses of a progesterone-containing oral dosage form and optionally a placebo dose of an oral dosage form. The kit can also include a set of instructions regarding use of the oral dosage forms as part of a regimen or other treatment event.

The plurality of progesterone-containing oral dosage forms can include oral dosage forms having different doses of progesterone. For example the kit can include a portion of the plurality of oral dosage forms that have 200 mg progesterone and another portion of the plurality of oral dosage forms that have 400 mg of progesterone. In other embodiments, the plurality of oral dosage forms can have the same dose of progesterone. The kit can be such that upon single dose administration of one of the progesterone-containing oral dosage forms to a woman, the progesterone-containing oral dosage form provides a ratio of serum progesterone $AUC_{12-24}$ (ng*h/mL) to administered dose (mg) of at least about $1 \times 10^{-07}$ and does not exceed about $8 \times 10^{-07}$ (ng*h/ml)/mg. The kit may further include one or more other components, including, but not limited to 1) instructions to enable those ordinarily skilled in the art to prepare a dosage form for immediate dispensing to the subject in need of; 2) one or more containers filled with one or more of the ingredients of the oral pharmaceutical dosage forms of the invention. Suitable containers include, for example, a bottle, a box, a blister card, a foil packet, or a combination thereof; 3) a tamper proof container or packaging; 4) other pharmaceutical dosage forms including other active agents; 5) Notice or printed instructions: in a form prescribed by a governmental agency regulating the manufacture, use, or sale of pharmaceuticals or biological products, which notice reflects approval by the agency of the manufacture, use, or sale for human administration to treat a condition that could be treated by oral progesterone therapy; 6) A "planner" for monitoring and tracking administration of the oral dosage forms; 7) Containers for storing and transporting the components of the kit; 8) Pregnancy test kits; 9) progesterone testing materials; 10) vitamins and/or nutritional supplements such as folates, omega fatty acids; 11) Anti-bacterial infection materials.

The pharmaceutical kits prepared using the oral dosage forms disclosed herein can be formulated to provide contraception to a woman or to be used for non-contraceptive treatment of a woman. In one embodiment, the kit can be formulated to provide contraception to a woman and the reversal of contraception in the woman can occur within about 4 days following cessation of use of the kit. In another embodiment, the kit can provide a lag time to withdrawal bleeding in a woman of no more than about 48 hours from the time of cessation of administration of the progesterone-containing dosage form. In one embodiment, the kit can be formulated for administration of an oral dosage once-a-day for a period of at least 28 days. In another embodiment, the kit can be formulated for administration of an oral dosage once-a-day for a period of at least 56 days. In another embodiment, the kit can be formulated for administration of an oral dose once-a-day for a period of at least 84 days. In some embodiments, the kit can include 1 to 7 placebo dosage forms. As set forth above in the definitions, a placebo dosage form is a dosage form that contains no progesterone. The kits of the present invention can include any of the progesterone-containing oral dosage forms disclosed herein. In one embodiment, the kit contains progesterone-containing oral dosage forms that are formulated to provide a monophasic, biphasic or triphasic progesterone dosing regimen. A monophasic progesterone dosing regimen is a dosing regimen in which a same dose of progesterone is administered everyday over a consecutive day administration period of 28 days, 56 days or 84 days. Accordingly, in one embodiment, when the kit is formulated to provide a monophasic regimen, the kit includes oral dosage forms that have identical doses of progesterone.

A biphasic progesterone dosing regimen includes an initial progesterone dose that is administered every day during an "initial phase" or "first phase" of the regimen that can last for a predetermined period of days. The regimen then includes a "second phase" in which a different dose of progesterone (usually, lower than the initial phase daily dosage amount) is administered for a predetermined period days. By way of example, a progesterone dose of 400 mg can be administered daily in the initial or first phase (can be day-1 to day-14) and a progesterone dose of 200 mg is administered daily in the "second phase" (day-15 to day 28). When a placebo (non-progesterone containing) dosage form is included in the kit for use from day 22 to day 28, then the second phase progesterone dosing may extend from day-15 to about day 21. This regimen is still "biphasic" in terms of progesterone dosing regimen. A "triphasic regimen" includes three different progesterone doses in each of three phases within a 28-day cycle. It can also be possible that the triphasic regimen includes two identical progesterone dosing phases separated by a different progesterone dosing phase. It should be noted that an additional active agent, such as for example estradiol, may optionally be included along with the progesterone-containing dosage forms for monophasic, biphasic and/or triphasic progesterone dosing regimen.

The progesterone-containing dosage forms disclosed herein can provide reduced dizziness associated with the oral administration of progesterone. A method of administering any of the oral dosage forms claimed herein to a subject is also contemplated. The reduction in dizziness associated with the administration can be quantified or measured by an increase in saccadic eye velocity (SEV) of the subject, as compared to the saccadic eye velocity of the subject when administered an equivalent dose of progesterone in dosage form that does not conform to the compositional requirements of the oral dosage forms disclosed herein.

The reduction in dizziness associated with the administration can be measured by any known method in the art including the measurement of saccadic eye velocity (SEV) of the subject. Saccadic Eye Velocity (SEV) is one method of measuring extent of dizziness. When progesterone is administered to a human subject orally, pregnane metabolite levels rise due to metabolism and lead to dizziness. A decrease in SEV can indicate that the subject is dizzy or sedated. When a subject is dizzy the saccadic eye velocity tends to be slower. Without wishing to be bound to the theory, the current inventive oral dosage forms can slowly release the progesterone at an rate such that a rapid increase in the serum concentration of pregnane metabolites is prevented. It is also within the scope of this invention that oral dosage form can provide a release rate such that the serum pregnane metabolites (e.g. allopregnanolone) level is maintained at low levels (typically, about 8 ng/mL or less for allopregnanolone) which levels can reduce anxiety and/or facilitate "positive mood".

In another embodiment, the progesterone-containing oral dosage forms and/or methods (regimen) of administration disclosed herein can provide several benefits to the user, particularly non-pregnant female users from adolescent age up to menopause. In addition to the highly effective, safe and easily reversible contraception, the said oral dosage forms and related methods (regimen) can provide one or more of the following significant benefits/improvements (≥20% difference) compared to the typical progestin (non-bioidentical progesterone)-containing contraceptive dosage forms: 1) better cycle control; 2) decreased risk of iron-deficiency anemia; 3) reduction in premenstrual syndrome; 4) reduced cyclic depression; reduction in the risks of functional ovarian cysts, benign breast cysts, fibroadenoma and ectopic pregnancy; 5) lower thrombolytic and vascular events risk; 6) reduced or no risk of loss of libido; 7) reduced or no negative effects on the carbohydrate and lipid metabolisms; 8) lower risk of adverse metabolic syndromes; 9) lower incidences of pill amenorrhea (Latent Fear of Pregnancy); 10) reduction in occurrences of mood swings/changes; 11) reduction in headache/migraine, acne formation, incidences of high blood pressure, metrorrhagia and irregular bleeding, nausea/vomiting; 12 reduction in breast pain, discomfort and/or tenderness; and 13) lower risk of breast cancer.

In a further embodiment, the significant advantages/improvements (with ≥20% difference) of the progesterone-containing oral dosage forms and related methods (regimen) of administration disclosed herein compared to the synthetic contraceptive pills include: 1) higher and specific selectivity to progesterone receptors; 2) least or no adverse-effects due to androgenicity (such as acne hirsutism etc.); 3) minimum impact on lipid profile; 4) reduced or no anti-androgenic and anti-mineralocorticoid activities resulting in lower risk of venous thrombosis and/or loss of libido, lower risk of body weight gain; 5) optimal half-life of the progesterone enabling reduced time (days) to fertility (reversibility of contraception) and also reduced or no risk to the fetus if pregnancy occurs; 6) reduced occurrences of pill amenorrhea.

In another embodiment, the progesterone-containing oral dosage forms and/or methods (regimen) of administration disclosed herein provides significant advantages/improvements (≥20% difference) to nursing mothers wishing to adopt supplemental contraception, in terms of least or no adverse effect on the child being nursed, compared. In another embodiment, the progesterone-containing oral dosage forms and/or methods (regimen) of administration disclosed herein which include estradiol, a significant improvement in menstrual cycle control can be achieved as compared to the typical combination contraceptive pills containing non-bioidentical progestogen and estrogen agents.

In a specific embodiment, the progesterone-containing oral dosage forms and related methods (regimen) of administration for contraception disclosed herein can provide significant advantages/improvements (≥20% difference) compared to an equivalent progesterone dose administered in the form of conventional progesterone-containing dosage forms (for e.g. capsule comprising micronized progesterone suspended in edible oil) including: 1) larger safety time window for a missed dose; 2) predictability in withdrawal bleeding; 3) reversibility to fertility; 4) lower fluctuation in the serum concentrations of progesterone and pregnane metabolites between consecutive dose administration.

EXAMPLES

The following examples are provided to promote a more clear understanding of certain embodiments of the present invention, and are in no way meant as a limitation thereon. The compositions may be suitably modified by a person skilled in the art to get dosage forms such as capsule, tablet, mould, beads, granules and the like. Note that, the progesterone in example oral dosage forms listed below can be either treated (milled, micronized, or nanosized) or untreated, as indicated, where not specified can be either.

Example 1

Progesterone Containing Oral Dosage Forms for Oral Delivery

Several progesterone-containing dosage forms are prepared using the components as set forth in Tables I-IV. The dosage forms are provided for ease of understanding the invention and are generally solid dosage forms such as a tablet. The dosage forms are prepared by mixing the release modulator, processing aids and the optional surfactant with progesterone to form a homogenous powder blend. The powder blend can be compressed to form tablets by direct compression or after dry or wet granulation process steps. In case of wet granulation, a solution of binder (such as PVP K30) can be used for granulation. The binder solution may optionally contain a portion (or all) of the amount of the surfactant, when a surfactant is present in the dosage form. Following granulation, the resultant product can be dried and compressed into tablets.

For instance, if desired, dosage forms can be prepared by wet granulation process using a binder solution of a 6-12% w/w Povidone K30 (a processing aid) in DI water. When a surfactant is present it can be present in the dry components or in the wet binder solution. For example, when a surfactant is present about 25-50% of the amount of the surfactant can be dissolved in the DI water. The release modifying (or release modulating) agent (if present), the remaining amount of the surfactant and filler/diluent (microcrystalline cellulose; processing aid) are homogenously blended with the progesterone in the shallow bowl of a conventional wet granulator (Diosna, Collette or equivalent) and granulated with the binder solution. The wet granulate is dried (e.g. in a tray dryer) to a moisture content of less than about 2% w/w. The dried granules are sized using a QaudroComill (or equivalent), mixed with process aids such as silicon dioxide and purified talc in a double cone blender, lubricated with magnesium stearate and/or stearic acid and finally compressed to get tablet dosage forms having required hardness (e.g. about 10-18 kP).

TABLE IA

| DOSAGE FORMS | | | | | | | | | | | |
|---|---|---|---|---|---|---|---|---|---|---|---|
| DOSAGE FORM # | 1 | 2 | 3 | 4 | 5 | 6 | 7 | 8 | 9 | 10 | 11 |
| | | | | | Component % w/w | | | | | | |
| Progesterone (treated) | 15-40 | 15-40 | — | 15-45 | 18-40 | 18-33 | 18-33 | 24 | 50 | 24 | 12 |
| Progesterone (untreated) | — | — | 15-40 | — | — | — | — | — | — | — | — |
| Hydrophilic Release Modulator (e.g. HPMC, HPC, CMC, methacrylates, PLGA) | 0 | 18 | 0-60 | 25-80 | 35-70 | 45-65 | 45-60 | 53 | — | 18 | 82 |
| Surfactant (e.g. polysorbate 80, polyoxyl 40 hydrogenated castor oil, Sodium Lauryl sulfate, Sodium docusate) | 0 | 25 | 25 | 0-25 | 0-25 | 0-20 | 5-10 | 6 | 0-25 | 0-25 | 5-10 |
| Processing Aids (e.g. filler, binder, lubricant etc.) | q.s. to 100% | q.s. to 100% | q.s. to 100% | q.s. to 100% | q.s. to 100% | q.s. to 100% | q.s. to 100% | q.s. to 100% | q.s. to 100% | q.s. to 100% | q.s. to 100% |

TABLE 1B

| DOSAGE FORMS WITH PHARMACOKINETIC RESULTS | | | | | | | | | | | |
|---|---|---|---|---|---|---|---|---|---|---|---|
| DOSAGE FORM # | 1 | 2 | 3 | 4 | 5 | 6 | 7 | 8 | 9 | 10 | 11 |
| SERUM PROGESTERONE (P) PK PARAMETERS, AFTER SINGLE DOSE (CONCENTRATIONS PER UNIT MEASURE INDICATED) | | | | | | | | | | | |
| $P\text{-}C_{24}$, [ng/mL] | <0.2 | <0.2 | <0.2 | >0.2 | >0.2 | >0.2 | >0.2 | 0.32 | <0.2 | <0.2 | <0.2 |
| $P\text{-}C_{36}$, [ng/mL] | <0.20 | <0.20 | <0.20 | ≥0.20 | ≥0.20 | ≥0.20 | ≥0.20 | ≥0.20 | <0.20 | <0.20 | <0.20 |
| $P\text{-}C_{max}$, [g/mL] | ≥10 | ≥10 | ≥10 | ≤10 | ≤10 | ≤10 | ≤10 | ≤10 | ≤10 | ≥10 | ≤10 |
| $P\text{-}C_{max}$ to $C_{24}$ | >10 | >10 | >10 | 1-10 | 1-10 | 1-10 | 1-10 | 1.44 | >10 | >10 | 1-3 |
| $P\text{-}AUC_{12\text{-}24}$, [ng*h/mL] | <2.5 | <2.5 | <2.5 | 3-6 | 3-6 | 3-6 | 3-6 | 4.5 | <2.5 | <2.5 | 0.5-2 |
| $P\text{-}AUC_{12\text{-}24}$/P-dose, [(ng*h/mL)/mg] | <0.004 | <0.004 | <0.004 | 0.005-0.03 | 0.005-0.03 | 0.005-0.03 | 0.005-0.03 | 0.0225 | <0.004 | <0.004 | <0.004 |

TABLE 1B-continued

DOSAGE FORMS WITH PHARMACOKINETIC RESULTS

| DOSAGE FORM # | 1 | 2 | 3 | 4 | 5 | 6 | 7 | 8 | 9 | 10 | 11 |
|---|---|---|---|---|---|---|---|---|---|---|---|
| P-dose/$C_{24}$, [mg/(ng/mL)] | >1000 | >1000 | >1000 | 100-1000 | 100-1000 | 100-1000 | 100-1000 | 628 | >1000 | >1000 | 1500-2500 |
| TOTAL PREGNANE (PG) METABOLITES (CONCENTRATIONS PER UNIT MEASURE INDICATED) | | | | | | | | | | | |
| PG-$C_{max}$, [ng/mL] | >10 | >10 | >10 | <10 | <10 | <10 | <10 | 3.03 | >20 | >10 | 1.0 |
| P-dose/PG-$C_{max}$ [mg/(ng/mL)] | <10 | <20 | <20 | 20-180 | 20-180 | 20-180 | 20-180 | 66 | <20 | <20 | 200 |
| PG-$C_{ave(0-24)}$ [ng/mL] | >2.5 | >2.5 | >2.5 | 0.5-2.0 | 0.5-2.0 | 0.5-2.0 | 0.5-2.0 | 1.75 | >2.5 | >2.5 | <0.5 |
| TOTAL ALLOPREGNANOLONE (AP) (CONCENTRATIONS PER UNIT MEASURE INDICATED) | | | | | | | | | | | |
| AP-$C_{max}$, [ng/mL] | >10 | >10 | >10 | 0.2-5.0 | 0.2-5.0 | 0.2-5.0 | 0.2-5.0 | 1.6 | >10 | >10 | <0.2 |
| AP-$C_{ave(0-24)}$, [ng/mL] | 1.5-4.0 | 1.5-4.0 | 1.5-4.0 | 0.3-1.45 | 0.3-1.45 | 0.3-1.45 | 0.3-1.45 | 0.85 | 1.5-4.0 | 1.5-4.0 | <0.3 |
| AP-$C_{max}$ to P-$C_{24}$ | >75 | >75 | >75 | 2-20 | 2-20 | 2-20 | 2-20 | 6.12 | >150 | >100 | >20 |
| P-dose/AP-$C_{max}$ [mg/(ng/mL)] | <20 | <20 | <20 | 50-300 | 50-300 | 50-300 | 50-300 | 126 | 11 | 20 | >300 |

Dosage forms 4-8 have levels of compositional components (progesterone, hydrophilic release modulator and surfactant, if present) that provide desired performance consistent with embodiments of the invention. These dosage forms contain progesterone in the range of 100-600 mg and can also contain an estrogen (0.010 to 0.1 mg of ethinyl estradiol, 0.05 to 5 mg of estradiol or estradiol valerate). Further, these dosage forms, when prepared without progesterone can function as placebo (with or without Estrogen). For multi-phasic applications, the dose of progesterone and/or estrogen can be varied in the dosage form as a component of a kit.

TABLE- IIA

DOSAGE FORMS

| DOSAGE FORM # | 12 | 13 | 14 | 15 | 16 | 17 | 18 | 19 | 20 | 21 | 22 |
|---|---|---|---|---|---|---|---|---|---|---|---|
| COMPONENT ( % w/w) | | | | | | | | | | | |
| Progesterone | 15-40 | 15-40 | 18-33 | 15-40 | 15-40 | 18-33 | 25 | 25 | 25 | 25 | 8 |
| Non-lipidic Lipophilic Release modulator (e.g. Ethyl cellulose cellulose acetate phthalate, sucrose acetate isobutyrate, shellac, etc.) | 8-35 | 10-20 | 10-20 | 5-30 | 8-20 | 8-20 | 5 | 5 | 55 | 5 | 40 |
| Hydrophilic Release Modulator (e.g. HPMC, HPC, CMC, methacrylates, PLGA) | — | — | — | 10-65 | 10-40 | 10-40 | 25 | — | — | 5 | 45 |
| Surfactant (e.g. polysorbate 80, polyoxyl 40 hydrogenated castor oil, Sodium Lauryl sulfate, Sodium docusate) | 0-25 | 0-25 | 4-10 | 0-25 | 0-25 | 4-10 | 6 | 0-25 | 6 | 0-25 | 6 |
| Processing Aids (e.g. filler, binder, lubricant etc.) | q.s. to 100% | q.s. to 100% | q.s. to 100% | q.s. to 100% | q.s. to 100% | q.s. to 100% | q.s. to 100% | q.s. to 100% | q.s. to 100% | q.s. to 100% | q.s. to 100% |

TABLE II B

IN VITRO RELEASE AND PHARMACOKINETIC RESULTS OF DOSAGE FORMS

| DOSAGE FORM # | | 12 | 13 | 14 | 15 | 16 | 17 | 18 | 19 | 20 | 21 | 22 |
|---|---|---|---|---|---|---|---|---|---|---|---|---|
| % Progesterone Released in vitro | 1 hour | <10 | <10 | <10 | <10 | <10 | <10 | 6 | 45 | 1 | 60 | <5 |
| | 3 hours | <25 | <25 | <25 | <25 | <25 | <25 | 18 | 75 | 6 | 100 | <15 |
| | 6 hours | ≤50 | ≤50 | ≤50 | ≤50 | ≤50 | ≤50 | 35 | 100 | 16 | 100 | 25 |
| | Time to 70% release | ≤12 h | ≤12 h | ≤12 h | ≤12 h | ≤12 h | ≤12 h | 10 h | <3 h | >24 h | <2 h | >>24 h |

SERUM PROGESTERONE (P) PK PARAMETERS, AFTER SINGLE DOSE ADMINISTRATION (CONCENTRATIONS PER UNIT MEASURE INTICATED)

| | 12 | 13 | 14 | 15 | 16 | 17 | 18 | 19 | 20 | 21 | 22 |
|---|---|---|---|---|---|---|---|---|---|---|---|
| $P\text{-}C_{24}$ [ng/mL] | >0.2 | >0.2 | >0.2 | >0.2 | >0.2 | >0.2 | >0.2 | <0.2 | <0.2 | <0.2 | <0.2 |
| $P\text{-}C_{max}$ [ng/mL] | <10 | <10 | <10 | <10 | <10 | <10 | >10 | <10 | >10 | <10 | <10 |
| $C_{ave(12\text{-}24\,h)}$ [ng/mL] | >0.11 | >0.11 | >0.11 | >0.11 | >0.11 | >0.11 | >0.11 | <0.11 | <0.11 | <0.11 | <0.11 |

TABLE IIIA

DOSAGE FORMS

| DOSAGE FORM # | 23 | 24 | 25 | 26 | 27 | 28 | 29 | 30 | 31 |
|---|---|---|---|---|---|---|---|---|---|
| COMPONENT ( % w/w) | | | | | | | | | |
| Progesterone | 15-40 | 15-40 | 18-33 | 15-40 | 25 | 25 | 25 | 25 | 8 |
| Lipidic Lipophilic Release modulator (e.g. carnauba waxes, hydrogenated castor oil, glyceryl distearate or combinations thereof) | 10-50 | 20-50 | 25-50 | 5-30 | 5 | 5 | 55 | 5 | 40 |
| Hydrophilic Release Modulator (e.g. HPMC, HPC, CMC, methacrylates, PLGA) | — | — | — | 15-65 | 35 | — | — | 8 | 40 |
| Surfactant (e.g. polysorbate 80, polyoxyl 40 hydrogenated castor oil, Sodium Lauryl sulfate, Sodium docusate) | 0-25 | 0-25 | 4-10 | 4-15 | 6 | 0-25 | 6 | 0-25 | 6 |
| Processing Aids | q.s. to 100% | q.s. to 100% | q.s. to 100% | q.s. to 100% | q.s. to 100% | q.s. to 100% | q.s. to 100% | q.s. to 100% | q.s. to 100% |

TABLE III B

IN VITRO RELEASE AND PHARMACOKINETIC RESULTS FOR DOSAGE FORMS

| DOSAGE FORM # | | 23 | 24 | 25 | 26 | 27 | 28 | 29 | 30 | 31 |
|---|---|---|---|---|---|---|---|---|---|---|
| % Progesterone Released in vitro | 1 hour | <10 | <10 | <10 | <10 | 6 | 70 | <10 | 50 | <10 |
| | 3 hours | <25 | <25 | <25 | <25 | 18 | 100 | 15 | 100 | <15 |
| | 6 hours | ≤50 | ≤50 | ≤50 | ≤50 | 35 | 100 | 20 | 100 | <20 |
| Hours to 70% Progesterone Released | T70% | ≤12 h | ≤12 h | ≤12 h | ≤12 h | 9.5 h | <2 h | >24 h | <3 h | >>24 h |

SERUM PROGESTERONE (P) PK PARAMETERS, AFTER SINGLE DOSE ADMINISTRATION

| | 23 | 24 | 25 | 26 | 27 | 28 | 29 | 30 | 31 |
|---|---|---|---|---|---|---|---|---|---|
| $P\text{-}C_{24}$ [ng/mL] | >0.2 | >0.2 | >0.2 | >0.2 | >0.2 | <0.2 | <0.2 | <0.2 | <0.2 |
| $P\text{-}C_{max}$ [ng/mL] | <10 | <10 | <10 | <10 | <10 | >10 | <10 | >10 | <10 |
| $C_{ave(12\text{-}24\,h)}$ [ng/mL] | >0.11 | >0.11 | >0.11 | >0.11 | >0.11 | <0.11 | <0.11 | <0.11 | <0.11 |

Dosage forms 12-18 and 23-27 have levels of compositional components (progesterone, hydrophilic release modulator and surfactant, if present) that provide desired performance consistent with embodiments of the invention. These dosage forms contain progesterone in the range of 100-600 mg and can also contain an Estrogen (0.005 to 0.1 mg of ethinyl estradiol, 0.05 to 5 mg of estradiol or estradiol valerate). Further, these dosage forms, when prepared without progesterone, can function as placebo (with or without estrogen). For multi-phasic applications, the dose of progesterone and/or estrogen can be varied in the dosage form as a component of a kit.

TABLE IV

DOSAGE FORMS WITH IN VITRO RELEASE AND PHARMACOKINETIC RESULTS

| DOSAGE FORM # | 32 | 33 | 34 | 35 | 36 | 37 | 38 | 39 | 40 | 41 | 42 |
|---|---|---|---|---|---|---|---|---|---|---|---|
| COMPONENT (% w/w) | | | | | | | | | | | |
| Progesterone | 15-40 | 15-40 | 15-40 | 18-33 | 18-33 | 18-33 | 25 | 25 | 25 | 18-33 | 18-33 |
| Estrogen (Ethinyl Estradiol) | 0.01-0.03 | — | — | 0.015-0.025 | — | — | 0.02 | — | — | 0.015-0.025 | — |
| Estrogen (Estradiol) | — | 0.1-0.3 | — | — | 0.15-0.25 | — | — | 0.2 | — | — | 0.15-0.25 |
| Estrogen (Estradiol Valerate) | — | — | 0.1-0.5 | — | — | 0.25-0.35 | — | — | 0.3 | — | — |
| Hydrophilic Release Modulator (e.g. HPMC, HPC, CMC, methacrylates, PLGA) | 20-80 | 20-65 | 20-65 | 45-65 | 45-65 | 45-65 | 53 | 53 | 53 | 10-40 | 15-40 |
| Lipophilic Release modulator (e.g. Ethyl cellulose cellulose acetate phthalate, sucrose acetate isobutyrate, shellac, carnauba waxes, hydrogenated castor oil, glyceryl distearate or combinations thereof etc.) | 0 | 5-30 | 0-30 | 0-30 | 0-30 | 0-30 | 0-30 | 0-30 | 0-30 | 5-30 | 5-30 |
| Surfactant (e.g. polysorbate 80, polyoxyl 40 hydrogenated castor oil, Sodium Lauryl sulfate, Sodium docusate) | 0-25 | 0-25 | 0-25 | 5-10 | 5-10 | 5-10 | 6 | 6 | 6 | 5-10 | 5-10 |
| Processing Aids (e.g. filler, binder, lubricant etc.) | q.s. to 100% | q.s. to 100% | q.s. to 100% | q.s. to 100% | q.s. to 100% | q.s. to 100% | q.s. to 100% | q.s. to 100% | q.s. to 100% | q.s. to 100% | q.s. to 100% |

Dosage Form 43: Peanut Oil, Lecithin and Micronized Progesterone Based Commercial Formulations such as Prometrium®.

Table IV exemplifies dosage forms having 100-600 mg progesterone combined with an estrogen (0.005 to 0.1 mg of ethinyl estradiol, 0.05 to 5 mg of estradiol or estradiol valerate). Further, these dosage forms, when prepared without progesterone can function as placebo (with or without estrogen). For multi-phasic applications, the dose of progesterone and/or estrogen can be varied in the dosage form as a component of a kit.

Example 2

In vitro Release of Progesterone Containing Compositions

To carry out in-vitro release of the dosage forms of the invention, a dosage form according to the present invention is placed into a stirred USP type 1 dissolution flask containing 900 mL of release medium comprised of DI Water dissolved with 2% w/v sodium lauryl sulfate. In the flasks, the dosage form is placed in a basket, so that all surfaces are exposed to the moving release media and the solutions are stirred at a rate of 100 rpm. Samples of the release medium are taken at periodic intervals. The concentration of dissolved drug in the dissolution medium is then determined by HPLC at a UV absorbance of 245 nm using a UV-Vis detector. Drug concentration is calculated by comparing UV absorbance of samples to the absorbance of drug standard solutions. The mass of dissolved drug in the dissolution medium is then calculated from the concentration of drug in the medium and the volume of the medium, and expressed as a percentage of the mass of drug originally present in the dosage form.

Oral dosage forms 8, 9, 11 and 43 (oil containing dosage form such as commercial Prometrium® manufactured by Abbott Laboratories) were tested in accordance with method described above. The resulting data is presented in the table below.

TABLE VI

Dissolution data summary of few example dosage forms

| Parameter | | Dosage form 8 | Dosage form 11 | Dosage form 09 | Dosage form 43 |
|---|---|---|---|---|---|
| % Progesterone Released | 1 hour | 6 | 2 | 80 | 12 |
| | 3 hours | 19 | 6 | 100 | 35 |
| | 6 hours | 39 | 15 | 100 | 61 |
| | 22 hours | 100 | 59 | 100 | 100 |
| Hours to 70% Progesterone Released | T70% | 10 h | 26 h | 0.75 h | 8 h |

Figure 4:
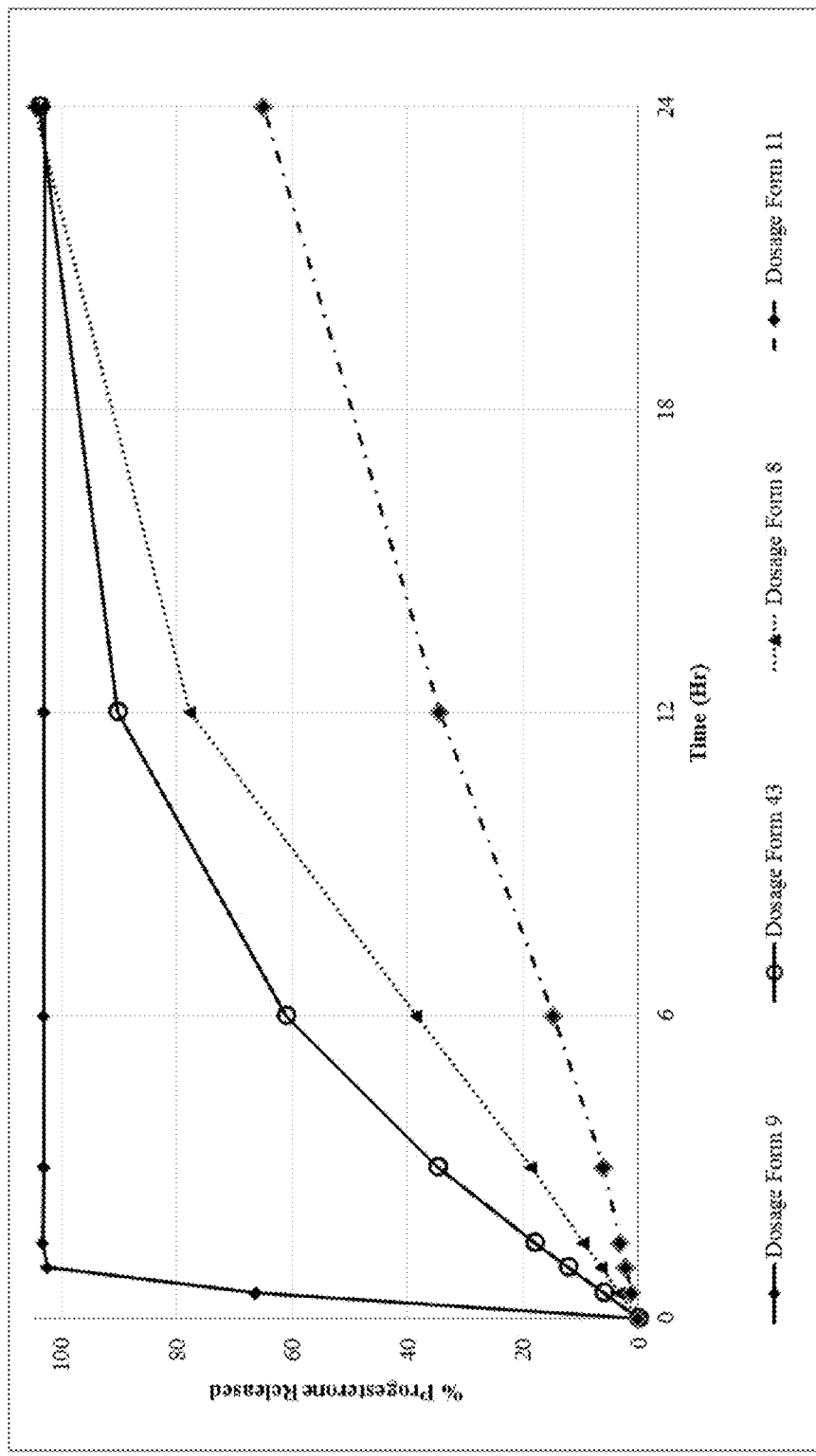
FIG. 4 shows comparative release profiles of oral dosage forms 9, 16, 26, and 43 upon placement of the oral dosage in a USP Type-1 dissolution apparatus in 900 mL of de-ionized water with 2.0% (w/v) of sodium lauryl sulfate at 100 rpm.
Figure 5:
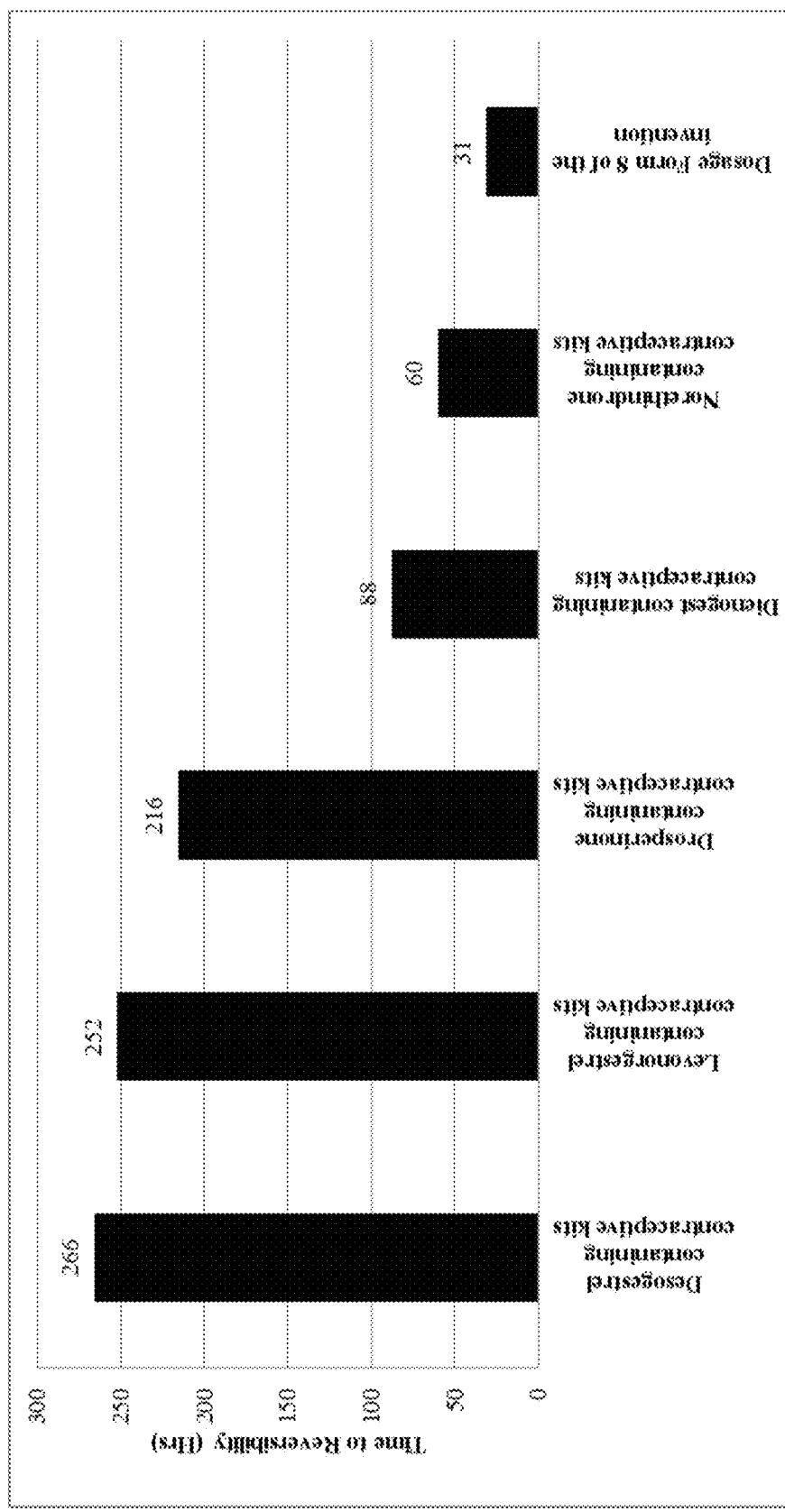
FIG. 5 shows a plot of the reversibility of contraception based on seven half-lives of progestogen in various commercially available contraceptive dosage form/kits containing progestins as well as that for an embodiment of the present invention of progesterone containing contraceptive dosage form/kit, following cessation of administration of the respective dosages.

As can be seen in TABLE VI, dosage forms 09 and 43 release higher levels of progesterone, while oral dosage form 11 is provides an excessively slow release rate in contrast to the desirable progesterone release profile exhibited by the oral dosage form 8. FIG. 4 shows the comparative dissolution profiles of these four oral dosage forms.

Example 3

Pharmacokinetic Testing of Progesterone Containing Oral Dosage Forms

Oral dosage forms 8, 9, 11 and 43 are administered to subjects in an open-label, randomized, single-dose, crossover study performed on 16 healthy volunteers. A total of 16 subjects complete the clinical phase of the study. In each period, subjects are housed from at least 20 hours before dosing until after the 24-hour blood draw. There is a 7-day washout between each dosing period. During the study the subjects are monitored for side effects like dizziness, drowsiness and sedation. The plasma progesterone analysis is carried out using LC-MS/MS method. Analysis of pregnane metabolites is also carried out by validated LC-MS/MS method. The $C_{max}$, $T_{max}$, $AUC_{0-t}$ and $AUC_{0-\infty}$ are calculated for progesterone in the plasma of the test subjects. Pharmacokinetic and statistical analyses are performed on the data obtained from the subjects. This data, in part, is contained in the following tables. The pharmacokinetic parameters are defined as follows:

$AUC_{0-t}$: The area under the plasma concentration versus time curve, from time 0 to the last measurable concentration of the administered drug, as calculated by the linear trapezoidal method.

AUC ($AUC_{0-\infty}$), $AUC_{inf}$: The area under the plasma concentration versus time curve from time 0 to infinity. AUC was calculated as the sum of the $AUC_{0-t}$ plus the ratio of the last measurable plasma concentration of the administered drug to the elimination rate constant.

$C_{max}$: The maximum measured plasma concentration of the administered drug.

$T_{max}$: The time at which the maximum measured plasma concentration of the administered drug is achieved.

$C_{ave(T1-T2)}$: The average plasma concentration of the analyte as determined by the ratio of $AUC_{(T1-T2)/t}$ wherein "t" is the corresponding time interval.

Mean: Average value of measured parameter of all individual subjects.

$AUC_{12-24}$: The area under the plasma concentration versus time curve from time 12 hours post dose to time 24 hours post dose.

P-$C_{24}$: Concentration of Progesterone at 24 hours after the administration of progesterone containing oral dosage form P-$C_{36}$: Concentration of Progesterone at 36 hours after the administration of progesterone containing oral dosage form The data from the analysis is given in Table VII.

TABLE VII

Pharmacokinetic Data of Single Dose Cross over PK Study in healthy volunteers

| | | DOSAGE FORM # | | | |
|---|---|---|---|---|---|
| | Units | 8 | 9 | 11 | 43 |
| SERUM PROGESTERONE (P) PK PARAMETERS, AFTER SINGLE DOSE | | | | | |
| P-$C_{24}$ | ng/mL | 0.32 | 0 | 0.11 | 0.15 |
| P-$C_{36}$ | ng/mL | 0.24 | 0 | 0.08 | 0.11 |
| P-$C_{max}$ | ng/mL | 0.46 | 3.81 | 0.15 | 2.09 |
| P-$C_{max}$ to $C_{24}$ | — | 1.44 | >10 | 1.44 | 14.27 |
| P-$AUC_{12-24}$ | ng * h/mL | 4.49 | 0.41 | 1.48 | 2.16 |
| P-dose/$C_{24}$ | mg/(ng/mL) | 628 | >1000 | 1903 | 1364 |
| TOTAL PREGNANE (PG) METABOLITES | | | | | |
| PG-$C_{max}$ | ng/mL | 3.03 | 28.38 | 1.0 | 18.19 |
| P-dose/PG-$C_{max}$ | mg/(ng/mL) | 66 | 7 | 200 | 11 |
| PG-$C_{ave(0-24)}$ | ng/mL | 1.75 | 4.69 | 0.45 | 4.03 |
| TOTAL ALLOPREGNANOLONE (AP) | | | | | |
| AP-$C_{max}$ | ng/mL | 1.59 | 17.69 | 0.12 | 11.54 |
| AP-$C_{ave(0-24)}$ | ng/mL | 0.83 | 2.94 | 0.22 | 2.23 |
| AP-$C_{max}$ to P-$C_{24}$ Ratio | — | 6.12 | >20 | 24.55 | 114.81 |
| P-dose/AP-$C_{max}$ | mg/(ng/mL) | 126 | 11 | 381 | 17 |

As can be seen, oral dosage forms 9, 11 and 43 lead to either high (9 & 43) or very low (11) progesterone $C_{max}$ values along with unsuitable levels of metabolites (9 & 43). While oral dosage form 8 provides suitable $C_{max}$ and $C_{24}$ values for both progesterone and metabolites so as to enable contraception, while minimizing the metabolites and related side effects.

Example 4

Steady State Simulation Following Single Dose to a Female Subject

Figure 2:
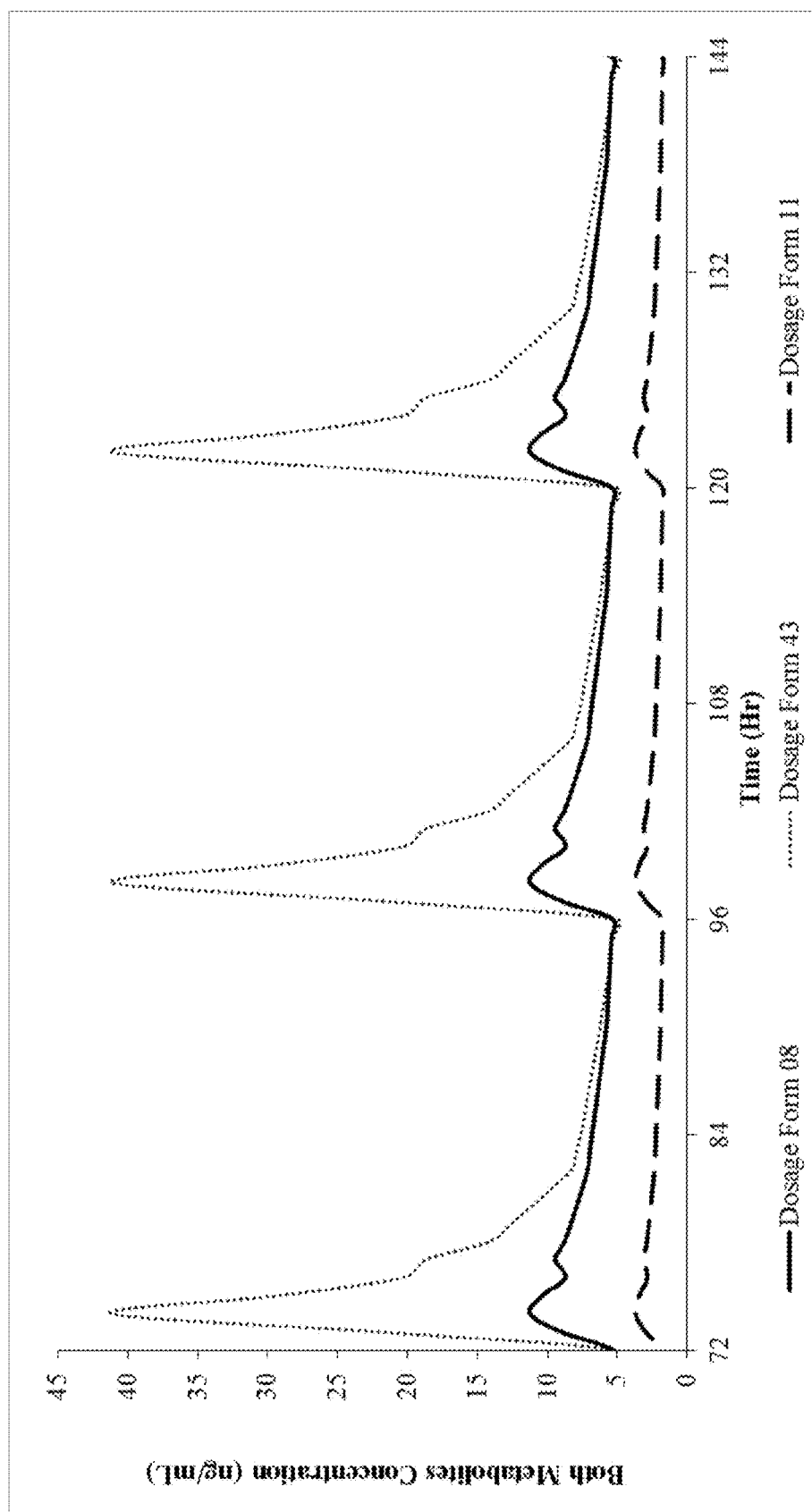
FIG. 2 shows simulated steady state concentrations of progesterone metabolites in vivo upon administration of dosage forms 8, 11 and 43, each dosage form containing 400 mg progesterone. Among the dosage forms administered dosage form 43 gives very high concentrations of metabolites while dosage form 11 gives very low levels of metabolites. Dosage form 8 maintains acceptable/desirable levels of metabolites while maintaining safe and effective concentrations of progesterone.
Figure 3:
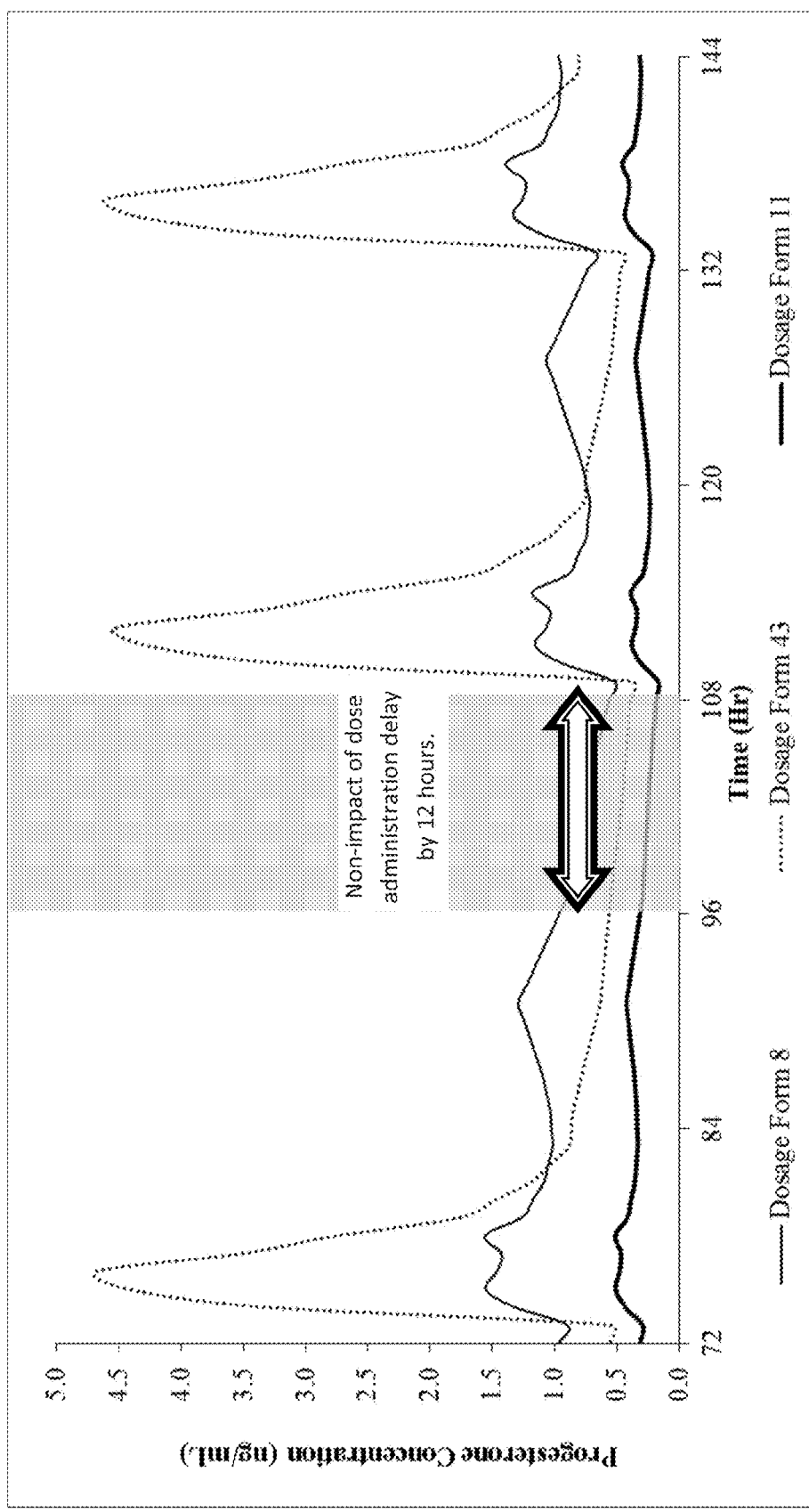
FIG. 3 shows simulated steady state concentrations of progesterone in vivo upon administration of different dosage forms 8, 11 and 43, each dosage form containing 400 mg progesterone. In particular, the steady state concentrations are shown when one of the dose administrations is delayed by 12 hours (i.e. at 108 hrs instead of 96 hrs). Among the dosage forms administered, dosage forms 11 and 43 have levels that drop below therapeutically effective concentrations when dose is delayed. In contrast, dosage form 8 maintains effective levels of progesterone thereby providing for significant window of safety and efficacy.

Simulated steady state data for single dose administration of various progesterone-containing oral dosage forms are prepared. FIG. 1 shows the comparative simulated steady state plasma progesterone concentration versus time profiles for a 400 mg progesterone dose with the Oral dosage forms 8, 11 and 43, following once daily administration. FIG. 2 shows the comparative total progesterone metabolites concentration profiles for the corresponding oral dosage forms. The simulated steady state plasma progesterone levels even after a "missed dose" is shown in FIG. 3, with the dose scheduled to be administered at 96 hours being delayed by 12 hours and being administered at 108 hours. As can be seen from the accompanying figures, the plasma progesterone levels and metabolites levels are consistently within the therapeutic and safety range for oral dosage form 8. Even when the dosage administration is delayed for 12 hours ("missed does"), oral dosage form 8 maintains the plasma progesterone level in the therapeutic range.

It is to be understood that the above-described various types of compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. An oral dosage form, for ongoing administration comprising:
    about 200 mg to about 600 mg a treated of natural progesterone at 15 weight/weight % (wt %) to 45 wt % of the dosage form;
    a pharmaceutically acceptable carrier; and
    a release modulator including a hydrophilic release rate modulator present in an amount of from 25 wt % to 80 wt % of the dosage form wherein said hydrophilic release rate modulator is carboxymethyl cellulose (CMC), hydroxypropyl cellulose (HPC), hydroxypropyl methyl cellulose (HPMC), hydroxyropyl methyl cellulose acetate succinate (HPMCAS), a methylacrylate, or a combination thereof;
    wherein the release modulator is present in an amount such that the ratio of release modulator to the amount of progesterone is about 0.75:1 to about 4:1 and wherein upon single dose administration to a non-pregnant woman in follicular phase the oral dosage form provides a serum progesterone $C_{24h}$ of at least 0.20 ng/mL.

2. The oral dosage form of claim 1, wherein upon single dose administration to a subject the oral dosage form provides a serum total pregnane $C_{max}$ of no greater than 40 ng/mL.

3. The oral dosage form of claim 1, wherein upon single dose administration to a subject the oral dosage form provides a serum progesterone $C_{max}$ of no greater than 10 ng/mL.

4. The oral dosage form of claim 1, wherein upon single dose administration to a subject the oral dosage form provides a serum progesterone $C_{24h}$ of 1.5 ng/mL or less.

5. The oral dosage form of claim 1, wherein the oral dosage form has an in vitro release rate such that, when measured using a USP Type-1 dissolution apparatus in 900 mL of de-ionized water with 2.0 % (w/v) of sodium lauryl sulfate at 100 rpm, about 10 wt % or less of the progesterone in the oral dosage form is released in the first 60 minutes and at least 70 wt % of the progesterone is released from the oral dosage form within 12 hours.

6. The oral dosage form of claim 1, wherein the progesterone is present in the oral dosage form in an amount of about 400 mg.

7. The oral dosage form of claim 1, wherein upon single dose administration to a subject the oral dosage form provides a serum progesterone $AUC_{12-24h}$ (ng*h/mL) to administered progesterone dose (mg) ratio of at least 0.005 (ng*h/mL)/mg.

8. The oral dosage form of claim 1, wherein upon single dose administration to a subject the oral dosage form provides a ratio of administered progesterone dose (mg) to serum progesterone $C_{24h}$ (ng/mL) of about 100 mg/(ng/mL) to about 1000 mg/(ng/mL).

9. The oral dosage form of claim 1, wherein the oral dosage form further includes a lipophilic release modulator present in an amount of about 8 wt % to about 50 wt % of the oral dosage form.

10. The oral dosage form of claim 9, wherein the lipophilic release modulator is non-lipidic release modulator and is present in an amount of about 8 wt % to about 35 wt % of the oral dosage form.

11. The oral dosage form of claim 9, wherein the lipophilic release modulator is a lipidic release modulator present in the amount of about 10 wt % to about 50 wt % of the oral dosage form.

12. The oral dosage form of claim 1, wherein the hydrophilic release modulator is present in an amount of 30 wt % to 70 wt %.

13. The oral dosage form of claim 1, wherein the oral dosage form is formulated for administration to a subject to provide contraception.

14. The oral dose form of clam 1, wherein the amount of the pharmaceutical acceptable carrier comprises from about 55 wt % to about 85 wt % of the oral dosage form.

15. The oral dosage form of claim 1, further comprising an estrogenic agent.

16. The oral dosage form of claim 15, wherein the estrogenic agent is selected from the group consisting of estradiol, conjugated estradiol, conjugated equine estrogens, and esterified estradiol.

17. The oral dosage form of claim 15, wherein the estrogenic agent is estradiol and is present in the oral dosage form in an amount of about 0.5 mg to about 2.5 mg.

18. The oral dosage form of claim 15, Wherein the estrogenic agent is ethinyl estradiol and is present in the dosage form in an amount of about 0.01 mg to about 0.1 mg.

19. The oral dosage form of claim 15, wherein the estrogenic agent is estradiol valerate and is present in an amount of about 1.5 mg to about 3 mg.

20. The oral dosage form of claim 15, wherein hydrophilic release rate modulator present in an amount of from 40 wt % to 60 wt % of the dosage form.

21. The oral dosage form of claim 15, wherein the oral dosage form further includes a lipophilic release modulator present in an amount of about 8 wt % to about 50 wt % of the oral dosage form.

22. The oral dosage form of claim 21, wherein the lipophilic release modulator is non-lipidic release modulator and is present in an amount of about 8 wt % to about 35 wt % of the oral dosage form.

23. The oral dosage form of claim 21, wherein the lipophilic release modulator is a lipidic release modulator present in the amount of about 10 wt % to about 50 wt % of the oral dosage form.

24. The oral dosage form of claim 15, wherein the hydrophilic release modulator is present in an amount of from 30 wt % to 70 wt % and a lipophilic release modulator present in an amount of about 5 wt % to about 30 wt % of the oral dosage form.

25. The oral dosage form of claim 15, wherein the oral dosage form is a tablet or a capsule.

26. The oral dosage form of claim 15, wherein the oral dosage form is formulated for contraceptive use in women.

27. An oral dosage form, comprising:
   about 200 mg to about 400 mg a treated of natural progesterone at 15 weight/weight % (wt %) to 45 wt % of the dosage form, and
   a pharmaceutically acceptable release modulator, including a hydrophilic release rate modulator present in an amount of from 25 wt % to 80 wt % of the dosage form wherein said hydrophilic release rate modulator is carboxymethyl cellulose (CMC), hydroxypropyl cellulose (HPC), hydroxypropyl methyl cellulose (HPMC), hydroxypropyl methyl cellulose acetate succinate (HPMCAS), a methylacrylate or a combination thereof;
wherein the release modulator is present in an amount such that the ratio of release modulator to the amount of progesterone is about 0.75:1 to about 4:1 and wherein upon dissolution of the oral dosage using a USP Type-1 dissolution apparatus in 900 mL of de-ionized water with 2.0% (w/v) of sodium lauryl sulfate at 100 rpm, less than 10 wt % of the progesterone is released from the dosage form after about 1 hour, 50 wt % or less of the progesterone is released in the first 6 hours and at least 70 wt % of the progesterone is released within 12 hours and wherein upon single dose administration to a non-pregnant woman in follicular phase the oral dosage form provides a serum progesterone $C_{24h}$ of at least 0.20 ng/mL.

28. The oral dosage form of claim 27, wherein the oral dosage form releases less than 25 wt % of progesterone in the first 3 hours.

29. The oral dosage form of claim 27, further comprising a lipophilic release modulator which is present in an amount of about 8 wt % to about 50 wt % of the oral dosage form.

30. The oral dosage form of claim 29, wherein the lipophilic release modulator is a non-lipidic release modulator and is present in an amount of about 8 wt % to about 35 wt % of the oral dosage form.

31. The oral dosage form of claim 29, wherein the lipophilic release modulator is a release modulator present in the amount of about 10 wt % to about 50 wt % of the oral dosage form.

32. The oral dosage form of claim 27, wherein the hydrophilic release modulator is present in an amount of from 30 wt % to 70 wt % and further comprises a lipophilic release modulator present in the amount of about 5 wt % to about 30 wt % of the oral dosage form.

33. The oral dosage form of claim 27, further comprising at least one surfactant.

34. The oral dosage form of claim 33, wherein the surfactant is a hydrophilic surfactant.

35. The oral dosage form of claim 34, wherein the hydrophilic surfactant is an anionic or non-ionic surfactant.

36. The oral dosage form of claim 34, wherein the hydrophilic surfactant is selected from the group consisting of sodium lauryl sulphate, polysorbate 80, sodium docusate, polyoxyl castor oils, polyoxyl hydrogenated castor oils, and mixtures thereof.

37. The oral dosage form of claim 33, wherein the surfactant comprises about 0.1 wt % to about 25 wt % of the oral dosage form.

38. The oral dosage form of claim 33, wherein the surfactant comprises about 4 wt % to about 10 wt % of the oral dosage form.

39. The oral dosage form of claim 27, wherein the oral dosage form is substantially free of edible oils having a carbon chain length of 12 to 18 carbons.

40. The oral dosage form of claim 27, wherein upon single dose administration to a subject the oral dosage form provides a progesterone $AUC_{12-24}$ of at least 3 ng*h/mL.

41. The oral dosage form of claim 27, wherein upon single dose administration to a subject the oral dosage form provides an allopregnanolone $C_{max}$ of not more than 10 ng/mL.

42. The oral dosage form of claim 27, further comprising an estrogenic agent.

43. The oral dosage form of claim 42, wherein the estrogenic agent is present in an amount such that the ratio of the amount of estrogenic agent (mg) to the amount (mg) of progesterone in the oral dosage form is about $3 \times 10^{-5}$:1 to about $3 \times 10^{-2}$:1.

44. The oral dosage form of claim 42, wherein estrogenic agent is selected from the group consisting of estradiol, ethinyl estradiol, estradiol valerate, and combinations thereof.

45. The oral dosage form of claim 27, wherein the oral dosage form is a capsule or a tablet.

46. The oral dosage form of claim 27, wherein the oral dosage form is a matrix tablet.

47. The oral dosage form of claim 27, wherein the dosage form is formulated for administration once every 24 hours.

48. The oral dosage form of claim 27, wherein the dosage form is formulated to provide contraception when administered daily from day-1 to at least day-21 of a 28 day menstrual cycle in a normal cyclic woman.

49. A pharmaceutical kit, comprising:
a plurality of doses of a progesterone-containing oral dosage form including about 200 mg to about 400 mg a treated of natural progesterone at 15 weight/weight % (wt %) to 45 wt % of the dosage form and release modulator, said release modulator including a hydrophilic release rate modulator present in an amount of from 25 wt % to 80 wt % of the dosage form wherein said hydrophilic release rate modulator is carboxymethyl cellulose (CMC), hydroxypropyl cellulose (HPC), hydroxypropyl methyl cellulose (HPMC), hydroxypropyl methyl cellulose acetate succinate (HPMCAS), a methylacrylate, or a combination thereof; and
optionally a placebo oral dosage form,
wherein the release modulator is present in the progesterone-containing oral dosage form in an amount such that the ratio of release modulator to the amount of progesterone is about 0.75:1 to about 4:1 and wherein upon single dose administration of one of the progesterone-containing oral dosage forms to a non-pregnant woman, the progesterone-containing oral dosage form provides a ratio of serum progesterone $AUC_{12-24}$ (ng*h/mL) to administered dose (mg) is at least about 0.005 and does not exceed about 0.03 (ng*h/mL)/mg and wherein upon single dose administration to a non-pregnant woman in follicular phase the oral dosage form provides a serum progesterone $C_{24h}$ of at least 0.20 ng/mL.

50. The pharmaceutical kit of claim 49, wherein the kit is formulated to provide contraception when administered to a woman.

51. The pharmaceutical kit of claim 49, wherein the kit is formulated for non-contraceptive treatment to a woman.

52. The pharmaceutical kit of claim 49, wherein the kit comprises 1 to 7 placebo oral doses.

53. The pharmaceutical kit of claim 49, wherein the progesterone-containing oral dosage form further comprises an estrogenic agent.

54. The pharmaceutical kit of claim 53, wherein the estrogenic agent is estradiol and is present in the oral dosage form in an amount of about 0.5 mg to about 2.5 mg.

55. The oral dosage form of claim 53, wherein the estrogenic agent is ethinyl estradiol and is present in the oral dosage form in an amount of about 0.01 mg to about 0.1 mg.

56. The oral dosage form of claim 53, Wherein the estrogenic agent is estradiol valerate and is present in the oral dosage form in an amount of about 1.5 mg to about 3 mg.

57. The pharmaceutical kit of claim 53, wherein the estrogenic agent is selected from the group consisting of estradiol, ethinyl estradiol, estradiol valerate, estriol, and combinations thereof.

58. The pharmaceutical kit of claim 49, wherein the progesterone-containing oral dosage forms are formulated for administration once every 24 hours.

59. The pharmaceutical kit of claim 49, wherein upon single dose administration of the progesterone-containing oral dosage form to a woman, the progesterone-containing oral dosage form provides a ratio of progesterone dose administered (mg) to serum progesterone $C_{24h}$ (ng/mL) of about 100 mg/(ng/mL) to about 1000 mg/(ng/mL).

60. The pharmaceutical kit of claim 49, wherein the kit is formulated for administration of an oral dose once a day for a period of at least 28 days.

61. The pharmaceutical kit of claim 49, wherein the kit is formulated for administration of an oral dose once a day for a period of at least 84 days.

62. The pharmaceutical kit of claim 49, wherein the oral dosage forms of the kit are formulated to allow for reversibility of contraceptive effective within 48 hours following cessation of administration of the oral dosage forms.

* * * * *